United States Patent
Milleret et al.

(10) Patent No.: US 10,385,170 B2
(45) Date of Patent: Aug. 20, 2019

(54) METHOD, DEVICE AND SYSTEM FOR SPATIALLY CONTROLLING THE FORMATION OF A HYDROGEL ELECTROCHEMICALLY

(71) Applicants: UNIVERSITAT ZURICH, Zurich (CH); ETH ZURICH, Zurich (CH)

(72) Inventors: Vincent Milleret, Zurich (CH); Benjamin R. Simona, Zurich (CH); Janos Voros, Zurich (CH); Martin Ehrbar, Wil/SG (CH)

(73) Assignee: UNIVERSITAT ZURICH, Zurich (CH)

( * ) Notice: Subject to any disclaimer, the term of this patent is extended or adjusted under 35 U.S.C. 154(b) by 278 days.

(21) Appl. No.: 15/025,559

(22) PCT Filed: Sep. 29, 2014

(86) PCT No.: PCT/EP2014/070820
§ 371 (c)(1),
(2) Date: Mar. 29, 2016

(87) PCT Pub. No.: WO2015/044426
PCT Pub. Date: Apr. 2, 2015

(65) Prior Publication Data
US 2016/0230197 A1    Aug. 11, 2016

(30) Foreign Application Priority Data

Sep. 29, 2013 (EP) .................... 13186561
Oct. 1, 2013 (EP) .................... 13186965

(51) Int. Cl.
| | | |
|---|---|---|
| C12P 7/18 | (2006.01) |
| C25B 3/00 | (2006.01) |
| C25B 3/10 | (2006.01) |
| C25B 9/12 | (2006.01) |
| C08G 65/08 | (2006.01) |
| C08G 65/26 | (2006.01) |
| C08G 65/32 | (2006.01) |
| C08J 3/075 | (2006.01) |
| C12N 11/04 | (2006.01) |
| C25B 11/02 | (2006.01) |
| C25B 11/04 | (2006.01) |

(52) U.S. Cl.
CPC .............. *C08J 3/075* (2013.01); *C08G 65/08* (2013.01); *C08G 65/2696* (2013.01); *C08G 65/32* (2013.01); *C12N 11/04* (2013.01); *C12P 7/18* (2013.01); *C25B 3/00* (2013.01); *C25B 3/10* (2013.01); *C25B 3/105* (2013.01); *C25B 9/12* (2013.01); *C25B 11/02* (2013.01); *C25B 11/04* (2013.01); *C08G 2210/00* (2013.01)

(58) Field of Classification Search
None
See application file for complete search history.

(56) References Cited

U.S. PATENT DOCUMENTS

| | | |
|---|---|---|
| 2002/0008038 A1 | 1/2002 | Heller et al. |
| 2011/0171239 A1 | 7/2011 | Kaplan et al. |
| 2013/0243693 A1 | 9/2013 | Omenetto et al. |

OTHER PUBLICATIONS

Kojic et al., "Ion electrodiffusion governs silk electrogelation", Soft Matter 8: 6897 (2012) (Year: 2012).*
Sanborn T J et al: "In situ crosslinking of a biomimetic peptide-PEG hydrogel via thermally triggered activation of factor XIII" Biomaterials, vol. 23, No. 13, Jul. 1, 2002 (Jul. 1, 2002), pp. 2703-2710.

* cited by examiner

*Primary Examiner* — Anand U Desai
(74) *Attorney, Agent, or Firm* — JMB Davis Ben-David

(57) ABSTRACT

The invention relates to a method, a device and a system for producing particularly a hydrogel (200) and for controlling an enzymatically catalyzed formation of a covalent bond in a solution, wherein said covalent bond is formed between a first compound (20) comprising a first moiety (21) and a second compound (22) comprising a second moiety (23), wherein the first and the second moiety (21, 23) are a substrate of an enzyme wherein said enzyme catalyzes the formation of a covalent bond between the first and the second moiety (21, 23), and wherein a voltage is applied to the solution for spatially controlling said formation, wherein said voltage is adjusted such that it induces electrolysis of said solution.

11 Claims, 18 Drawing Sheets

METHOD, DEVICE AND SYSTEM FOR SPATIALLY CONTROLLING THE FORMATION OF A HYDROGEL ELECTROCHEMICALLY

CROSS-REFERENCE TO RELATED APPLICATIONS

This is the U.S. National Stage of International Application No. PCT/EP2014/070820 filed Sep. 29, 2014, which was published in English under PCT Article 21(2), and which in turn claims the benefit of European Patent Application No. 13186561.0 filed on Sep. 29, 2013, and European Patent Application No. 13186965.3 filed on Oct. 1, 2013.

The invention relates to a method, a device and a system for spatially and locally controlling a formation of a chemical link between a first and a second chemical compound in solution, particularly catalyzed by means of an enzymatic reaction and wherein the invention can particularly be used for producing a spatially structured hydrogel.

Three-dimensional (3D) engineered tissues are largely desirable to allow physiological studies and the development of regenerative therapies. Most of the recent attempts to build tissue mimetics are based on the culture of cells in extracellular matrix (ECM) hydrogels. In contrast to the inherent biological properties of natural hydrogels, synthetic hydrogels such as poly(ethylene glycol) (PEG) have no intrinsic interaction with biological systems, hence don't trigger—nor are affected by biological processes. However, the ability to precisely tailor the physical properties and the molecular architecture together with the selective introduction of biological functional molecules, namely proteolytic sites, cell adhesion sites and other biological cues makes PEG hydrogels an ideal platform for the emulation of naturally occurring ECM [1].

It is known that there are modular-designed PEG hydrogels, which are polymerized by a Factor XIII (FXIII)-mediated transglutamination (TG) reaction and thus are referred to as TG-PEG hydrogels [2]. During the FXIII-mediated crosslinking of the Glutamine-PEG (Gln-PEG) and the Lysine-PEG (Lys-PEG) precursors, various Gln- and Lys-tagged peptides and proteins can be covalently bound to the forming matrix [3, 4]. The enzymatic cross-linking reaction allows the site specific, orthogonal integration of bioactive molecules under physiological conditions to provide various functionalities [5, 6].

Although the ability to chemically functionalize PEG hydrogels represents an achievement, controlling the spatial chemical composition is necessary to engineer synthetic hydrogels mimicking the natural ECM [7, 8]. Techniques including casting [9], additive manufacturing (e.g. printing and layer-by-layer deposition) [10], photo-patterning [7, 11] and microfluidics [12] are amongst the techniques successfully used to produce 3D structured hydrogels with spatial control of the morphogenetic cues.

One of the main challenges in the additive manufacturing of soft hydrogels remains the optimization of the depositing material's mechanical properties to achieve good deposition control [13]. Electrochemical polymerization (e.g. oxidative polymerization) has the considerable advantage of being inherently independent of the polymer mechanical properties and was successfully used to locally control the polymerization of polyaniline [14], polypyrroles [15, 16], polyacrylates [17] and other electroactive polymers [18] for applications spanning from organic electronics to organic film deposition on biomedical implants [16].

Therefore, the problem underlying the present invention is to provide a method, a device and a system allowing the spatial control of formation of a covalent bond particularly for use in a linking reaction for a hydrogel and particularly to produce spatially controlled microenvironments.

This problem is solved by a method, a device, and a system described and claimed below. Preferred embodiments are stated in the sub claims.

According to claim 1, a method for controlling a linking reaction in a solution in proximity of a first electrode alters the pH of the solution locally for controlling said linking reaction in the proximity of said electrode by applying an electrolysis-inducing electrical current to the solution via said first electrode.

In order to induce electrolysis in the solution particularly a second electrode is provided.

The first electrode can assume anodic polarization or cathodic polarization, turning it into an anode or a cathode. A second electrode would assume the opposite polarity of the first electrode.

A linking reaction particularly refers to the chemical linking particularly via the formation of a covalent bond between two chemical compounds, particularly a first and a second compound comprising a first and a second moiety between which the link and particularly the covalent bond is established.

Generally, according to an embodiment of the invention, one or several parameters of the linking process are changed during the linking process (this applies to all embodiments of the present invention).

Particularly, one or a selection of the following parameters can be changed during the linking process:
- the composition of the crosslinking solution (e.g. buffer, enzymes, substrate of the enzyme, the used polymers and/or their functional groups),
- the position of the electrodes,
- the applied currents or voltages, and/or
- the duration of the (linking) process, wherein the linking process can also be interrupted, e.g. for changing parameters. This specifically covers an embodiment of the present invention where a previously prepared (hydro)gel (either created using the method according to the invention or any other gelation process) is locally functionalized. In a preferred embodiment of the invention a spatially structured hydrogel is formed by said linking reaction, wherein said hydrogel is particularly formed by local inhibition of the linking reaction, wherein said inhibition is particularly controlled by altering said pH locally, particularly such that said altered pH affects the enzymatic activity of an enzyme in the solution, and wherein particularly said enzyme is converting a first and a second moiety comprised by a first and a second compound in the solution to said hydrogel by means of forming a covalent bond between said first and second moiety.

A spatially structured hydrogel is particularly a hydrogel that has a consistency that varies in space. Such structures comprise particularly micro-channels or cavities particularly in the µm to mm range. Furthermore a spatially structured hydrogel comprises locations where despite there was solution present at these locations during formation of the hydrogel and wherein said solution comprised all necessary precursors, as for example the first and second chemical compound comprising the first and second moiety and an enzyme, the formation of the hydrogel was particularly inhibited in these location, such that at these location no hydrogel was formed and thus a spatially structured hydrogel is obtained.

Furthermore the term "spatially structured" also refers particularly to the spatially controlled deposition of chemical compounds particularly in and within a hydrogel, particularly for providing a biological microenvironment.

In another preferred embodiment of the invention the linking reaction is spatially and/or temporally confined by means of adjusting the magnitude and direction of the electrical current flowing through the solution.

According to claim 4, a method for controlling an enzymatically-catalysed formation of a covalent bond in a solution is claimed, particularly using the method according to the invention described above, wherein said covalent bond is formed between a first compound comprising a first moiety and a second compound comprising a second moiety, wherein the first and the second moiety are a substrate of an enzyme wherein said enzyme catalyzes the formation of a covalent bond between the first and the second moiety, and wherein a voltage is applied to the solution for spatially controlling said formation, wherein said voltage is adjusted such that it induces electrolysis of said solution, wherein said electrolysis induces a spatial pH distribution in said solution, said distribution being aligned particularly along the gradient of the voltage induced electric field, such that the particularly pH-dependent enzymatic activity of said enzyme is spatially controlled or inhibited or promoted or activated.

Furthermore modes of controlling the enzymatically-catalysed formation of said covalent bond comprise particularly inhibition, promotion, activation and/or changing the enzymatic activity of the enzyme, particularly the rate constant of the enzymatic reaction.

In a preferred embodiment of the invention said enzyme is an aminoacyltransferase (E. C. 2.3.2.), particularly a: transglutaminase (E. C. 2.3.2.13), more particular factor XIIIa (described by the UniProt Nr: P00488) or precursor thereof, the first moiety is an acyl, particularly an amide, and the second moiety is an amine. Preferably, non-limiting examples for such first and second moiety can be taken from Example 7 below.

FXIIIa for example uses a free amine group (e.g., protein- or peptide-bound lysine) and the acyl group at the end of the side chain of protein- or peptide-bound glutamine.

UniProt numbers refer to entries in the UniProt Knowledgebase.

The E. C. number refers to the so-called Enzyme Commission number that is a numerical classification scheme for enzymes.

According to an embodiment of the present invention, the first and/or second compound consists of or comprises a polymer, wherein said polymer is a natural polymer, particularly one of the following polymers: fibrin, alginate, chitosan, hyaluronic acid, chondroitin sulfate, heparin; or a synthetic polymer, particularly one of the following polymers: polyethylene glycol (PEG), polyactic acid, SU-8; or any polymer consisting of—or including—a combination of monomers, e.g. of dopamine, amine-containing groups such as lysine, cathecols, phosphate containing groups, thiol containing groups, alcohol containing groups, active esters and any polymer or dendrimer containing any of said groups (e.g. Hybrane, Boltorn).

According to a preferred embodiment of the present invention the first compound and/or the second compound comprises polyethylenglycol (PEG), particularly PEG with a molar weight in the range of 4000 to 100000 Dalton, particularly 40000 Dalton, and wherein said PEG is an unbranched or branched PEG and wherein the branched PEG comprises particularly 2, 3, 4, or 8 arms.

For instance in some embodiments the branched particularly the eight-armed PEG comprises a first or second chemical moiety on particularly each branch or arm of the PEG.

In another preferred embodiment of the invention the formation of the covalent bond is a condensation reaction, a ligation reaction, a cross-linking reaction or a polymerization reaction.

The term "polymerization" in the context of the present specification particularly refers to a process of reacting monomer molecules together in a chemical reaction to form polymer chains or three-dimensional networks.

The term "ligation reaction" in the context of the present specification particularly refers to the formation of a covalent bond between two molecules such as amino acids or nucleotides.

The term "cross-linking" in the context of the present specification particularly refers to the formation of a bond that links one polymer chain to another.

The term "condensation reaction" in the context of the present specification particularly refers to a chemical reaction in which two molecules or moieties combine to form a larger molecule, together with the loss of a small molecule. Examples for such small molecules include water, hydrogen chloride, methanol, ammonia, or acetic acid.

According to a preferred embodiment of the invention the voltage is induced via electrodes in said solution, and wherein the voltage is adjusted such that the pH of the solution in proximity of the electrode particularly lies within the range from 1 to 14, particularly 5 to 11.

In a preferred embodiment of the invention the enzymatic activity of the enzyme, particularly of the transglutaminase, particularly of FXIIIa, is locally inhibited, reduced or promoted depending particularly on the magnitude, polarity of the voltage applied to the solution, and/or the pH of said solution prior to the application of said voltage.

According to a preferred embodiment of the present invention the solution comprises a third compound comprising a third moiety, particularly an amide and/or an amine, wherein said third moiety is convertible by said enzyme with the respective first or second moiety, and wherein said third compound is particularly a bioactive molecule, particularly a growth factor, particularly such as platelet-derived growth factor (PDGF), vascular endothelial growth factor (VEGF), fibroblast growth factor (FGF), neural growth factor (NGF) and others, or cytokines (e.g. interleukins), affinity linkers (e.g. streptavidin-biotin, ZZ linker, histamine linker), short peptides (e.g. RGD, YIGSR), or proteins and protein fractions (e.g. Laminin, Fibronectin, Fibrinogen, Heparin).

The term "amide" in the context of the present specification particularly refers to a compound comprising an amide ($-CONR_2$, wherein each R can independently from the other be hydrogen or an alkyl).

The term "amine" in the context of the present specification particularly refers to a compound comprising an amine group ($-NR_2$, wherein each R can independently from the other be hydrogen or an alkyl).

In one claim, a method is described for providing a spatially structured hydrogel, particularly using the method according the invention described above, wherein a first compound comprising a first moiety and a second compound comprising a second moiety are linked into a spatially structured hydrogel by formation of a covalent bond between the first and the second moiety of the first and the second compound, and wherein a voltage is applied to a solution comprising the first and the second compound for spatially controlling said formation, wherein said voltage is adjusted such that it induces electrolysis of said solution.

In a preferred embodiment of the invention the linking reaction, particularly the cross-linking reaction a enzymatically catalysed, wherein the first moiety and the second moiety are a substrate of an enzyme, wherein the enzyme is particularly an aminoacyltransferase, particularly a transglutaminase, more particular factor XIIIa or a precursor thereof, and wherein the first moiety is particularly an amine and wherein the second moiety is particularly an amide.

According to a further aspect of the invention the pH of the solution is controlled such that the linking reaction is controlled particularly inhibited, promoted, activated or reduced such that the hydrogel exhibits at least in some regions of the hydrogel, particularly on interface regions of the hydrogel, sparsely linked first and second moieties such that particularly an increased cell permeability is achieved. In other words, the present method of the local inhibition of the polymerization can be used to create softer interfaces (e.g. less cross-linked polymer) for increased cell permeability.

Also described is a device for generating a hydrogel, particularly using the method according to the invention, wherein said device comprises a reaction chamber that is designed to hold a solution, and a first and a second electrode arranged at the reaction chamber, and particularly a voltage source being designed to apply a pre-defined voltage to said electrodes, so as to induces electrolysis in said solution, particularly so as to control a linking reaction in said solution by locally altering the pH of the solution. The concept of a first and a second electrode may particularly also mean that there is one electrode, wherein the other electrode (e.g. counter electrode) may be formed or comprised by another part of the device such as a wall or bottom of the reaction chamber (or even another electrode). Further, it is also possible to have a plurality of electrodes at which the linking reaction is to be controlled (see above).

In a preferred embodiment of the invention the first and/or second electrode is designed to be moved non-destructively with respect to the reaction chamber and/or released from the reaction chamber, particularly so as to remove the first and/or second electrode from the hydrogel.

It is for example possible to introduce said electrodes to the reaction chamber without destroying or damaging the chamber. It is also possible to remove an electrode from said chamber without damaging the device.

Particularly when the inhibition of the formation of a hydrogel in the proximity of an electrode is conducted according to the invention, said electrode is removable from said hydrogel in the reaction chamber without damaging/ straining or destroying said hydrogel.

Therefore particularly structures such as for example micro-channels, indentations and others can be formed according to the invention, by particularly inhibiting the formation of the hydrogel in said particular locations. Furthermore it is possible to generate hydrogel and to remove the electrodes destruction-free, as the formation of the hydrogel is inhibited or strongly reduced in proximity of at least one electrode.

Particularly a set of auxiliary components comprising tubing to access the reaction chamber particularly embedded in the electrode structure, membranes to separate the electrodes and a container to separate the hydrogel from the external environment can be comprised by the reaction chamber device according to the invention.

According to a preferred embodiment of the invention the first and/or second electrode comprises a metal, particularly tungsten, a semiconductor, a conductive polymeric material, or a combination of these materials.

The first electrode can assume anodic polarization or cathodic polarization, turning it into an anode or a cathode. The second electrode would assume the opposite polarity of the first electrode.

In a preferred embodiment of the invention the first and/or second electrode comprises a surface, wherein said surface comprises a region comprising a two-dimensional and/or three-dimensional structure wherein said structure being designed to act as a template for structuring the hydrogel by spatially controlling, particularly inhibiting or promoting, the hydrogel formation, particularly in the proximity of the structure, particularly when said pre-defined voltage is applied to said electrodes.

In another preferred embodiment of the invention the first and/or second electrode is formed as an elongated element, particularly as a wire, wherein said wire is particularly designed such that if the voltage is applied between the first and second electrode the formation of the hydrogel is inhibited, reduced or promoted in a proximity of the electrodes, wherein if the formation of the hydrogel is inhibited or reduced a hydrogel comprising a hollow channel can be formed, when the electrode is removed from said hydrogel.

According to a preferred embodiment of the present invention the first and the second electrode are designed to induce an electrical current density between 0 and ±100 $\mu A/mm^2$ in said solution in the reaction chamber.

In a preferred embodiment of the invention the first and/or second electrode comprises a cavity and/or a channel that are designed to hold and/or transport a liquid.

Such cavities or channels might act as a microfluidic device, where liquids can be handled and flown through for various purposes, but particularly for delivering said liquid to the solution or the formed hydrogel. Furthermore such a liquid might contain biological cells that are introduced via said electrode in the hydrogel particularly after or during formation.

According to yet another aspect of the present invention the first and/or second electrode is designed as a conductive scanning probe, particularly as an electrochemical atomic force microscope probe or a glass micro-electrode, wherein said conductive scanning probe particularly comprises a scanning tip that is preferably designed such that when a voltage is applied to the conductive scanning probe the electrical field will be highest in the proximity of the scanning tip, and wherein preferably said scanning probe is designed to be moveable, e.g. three-dimensionally movable, with respect to the reaction chamber (or hydrogel residing in the reaction chamber).

The scanning probe may be arranged at, in or on the reaction chamber, particularly in an interior of the reaction chamber, and may be removable from the reaction chamber.

Preferably, the scanning probe is movable by means of an actuator such as a known scanning stage, particularly an atomic force microscope stage.

According to a further aspect of invention a system for generating a spatially structured hydrogel is provided, comprising a device according to the invention, wherein the system further comprises said solution for generating a hydrogel and/or a hydrogel that is placed in said reaction chamber of the device according to the invention.

Some of the above stated embodiments or aspects of the invention may be cast into claims as follows:

One claim may be directed to a device characterized in that the first and/or second electrode (11, 12) comprises a surface, wherein said surface comprises a structure being designed to act as a template for structuring the hydrogel (200) by spatially controlling, particularly inhibiting or promoting, the hydrogel (200) formation, particularly in the proximity of the first and/or second electrode (11, 12), particularly when said pre-defined voltage is applied to said electrodes (11, 12).

Another claim may be directed to a device characterized in that the first and/or second electrode (11, 12) is formed as an elongated element, particularly as a needle or a wire.

Another claim may be directed to a device characterized in that the first and the second electrode (11, 12) are designed to induce an electrical current density between 0 and ±100 $\mu A/mm^2$ in said solution in the reaction chamber (100).

Another claim may be directed to a device characterized in that the first and/or second electrode (11, 12) comprises a cavity and/or a channel that are designed to hold and/or transport a liquid.

Another claim may be directed to a device characterized in that the first and/or second electrode (11, 12) is designed as a conductive scanning probe, particularly as an electrochemical atomic force microscope probe or a glass microelectrode, wherein said conductive scanning probe particularly comprises a scanning tip (121), particularly for locally (e.g. namely at the tip) controlling/influencing said solution/formation of said hydrogel as described herein, wherein said tip is particularly designed such that when a voltage is applied to the conductive scanning probe the electrical field will be highest in the proximity of the scanning tip (121), and wherein particularly said scanning probe is (e.g. three-dimensionally) movable, particularly in an interior (102) of the reaction chamber (100).

Another claim may be directed to a system comprising a device as described and wherein the system further comprises said solution for generating a hydrogel (200) and/or a hydrogel (200) that is placed in said reaction chamber (100) of the device.

Further features and advantages of the invention shall be described by means of a detailed description of embodiments with reference to the Figures, wherein FIG. 1 shows a perspective view of a device according to the invention;

Figure 1:
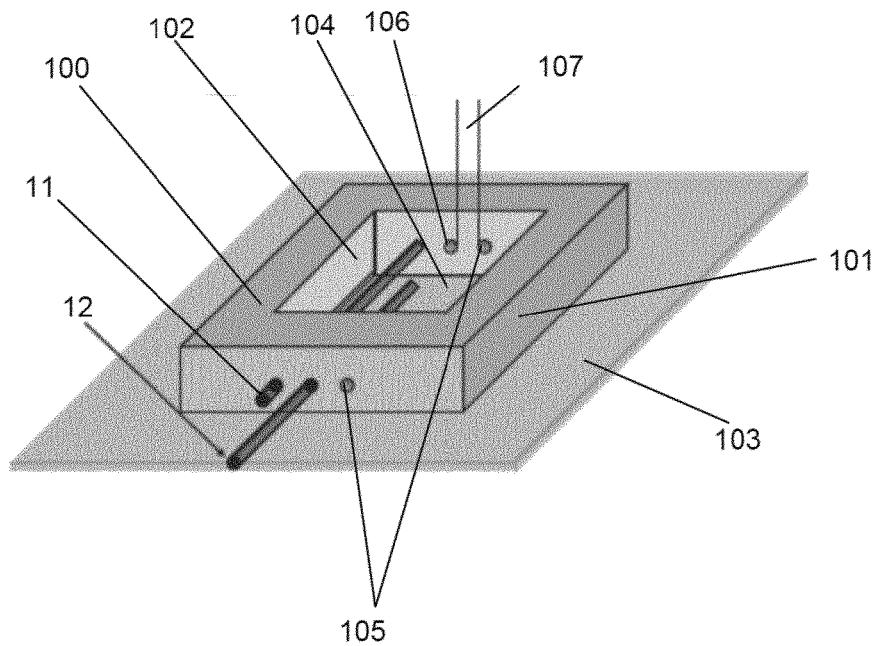

In FIG. 1 to FIG. 5 different embodiments and views of a device for conducting the method according to the invention is depicted. In Example 6 the preparation of such a device according to the invention is described.

The device features a reaction chamber 100, comprising a chamber wall 101 that surrounds an inside 102 of the reaction chamber 100, a first electrode 11 that is designed to be anodically or cathodically polarized by applying a voltage between said first electrode 11 and a second electrode 12 arranged at the reaction chamber 100, wherein said second electrode 12 assumes the opposite polarity of the first electrode 11 when the method according to the invention is conducted in the reaction chamber 100.

The reaction chamber 100 is particularly made of polydimethylsiloxane (PDMS) and is placed on a solid support 103. The inside 102 of the reaction chamber 100 is designed to hold a liquid, particularly a solution comprising precursors for a hydrogel. Furthermore the reaction chamber 100 is located on top of the solid support 103. The solid support 103 is preferably made of glass and is particularly a coverslip for use on a microscope. In a preferred embodiment of the invention said glass substrate 103 is a bottom 104 of the reaction chamber 100. The reaction chamber 100 can be bound to the coverslip 103 by surface plasma activation. The reaction chambers 100 volume in which the hydrogel precursors can be poured is approximately 50 μL.

In the embodiment of the invention in FIG. 1 the first and second electrode 11, 12 are designed as straight wires, particularly Tungsten-wires that run parallel to each other through the reaction chamber 100, particularly having the same distance from the bottom 104 of the reaction chamber 100.

Both electrodes 11, 12 particularly extend through the reaction chamber 100 connecting and penetrating the chamber wall 101 on two opposite sides of the reaction chamber 100.

The first electrode 11 and second electrode 12 preferably have a diameter within the range from 50 μm to 0.5 mm.

Furthermore the reaction chamber 100 can contain two opposite openings 105 in the chamber wall 101 suitable to house a third electrode 13. Said third electrode 13 being preferably designed as a wire, preferably like the first and second electrode 11, 12, and extending parallel to the first and second electrode 11, 12, wherein the distance 107 between the opening 106 for receiving the second electrode 12 and the opening 105 receiving the third electrode 13 is preferably 1 mm on each side of the reaction chamber 100. But may also be smaller or larger.

Figure 2:
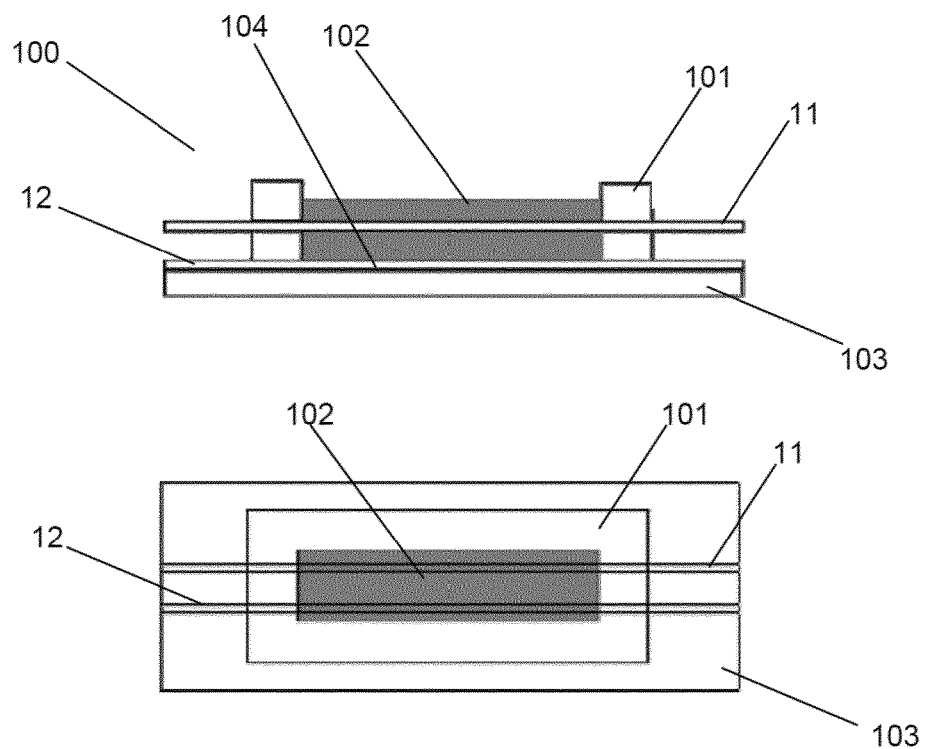
FIG. 2 shows a schematic view of a device according to the invention.

FIG. 2 shows another embodiment according to the invention. The upper panel shows a side view of the device according to the invention and the lower panel shows a top view of the device according to the invention.

It can be seen that the second electrode 12 is arranged closer to and particularly on the bottom 104 of the reaction chamber 100 in this embodiment. Otherwise said embodiment has preferably an analogue architecture as the embodiment depicted in FIG. 1.

Figure 3:
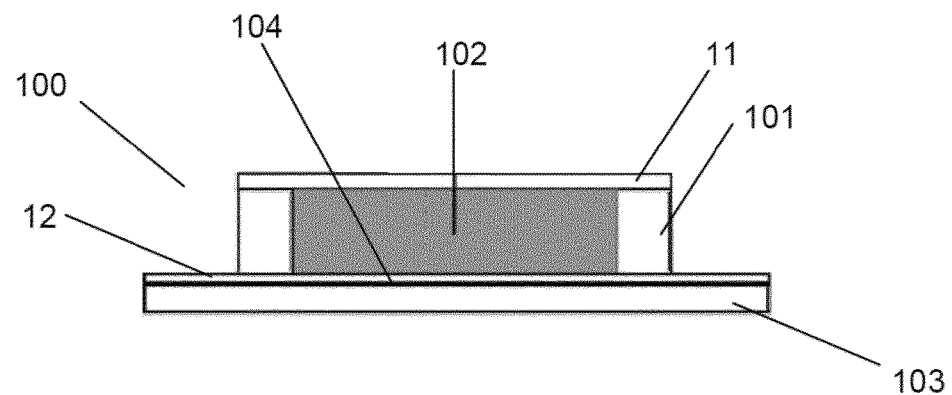
FIG. 3 shows a schematic view of a device according to the invention.
Figure 3:
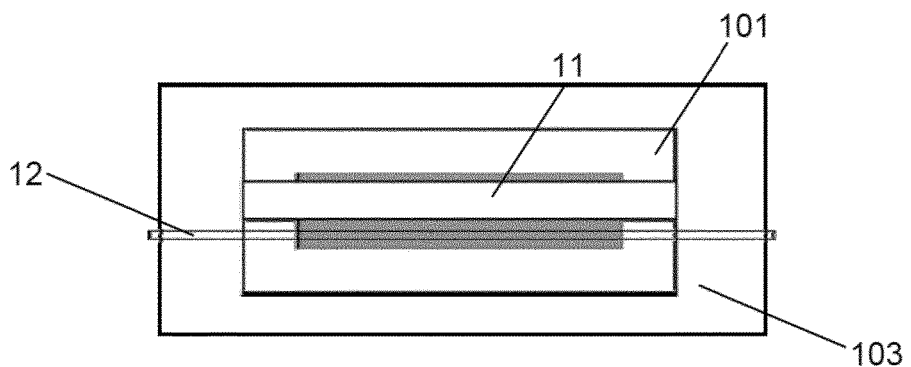

FIG. 3 shows another embodiment according to the invention. The upper panel shows a side view of the device according to the invention and the lower panel shows a top view of the device according to the invention.

The embodiment depicted in FIG. 3 features the first electrode 11 arranged on an upper end of the chamber wall 101, so that it covers the reaction chamber 100 at least partially. Furthermore the first electrode 11 has a rectangular contour. Other aspects of this embodiment are realized analogous to the embodiments shown in FIGS. 1 and 2.

Figure 4:
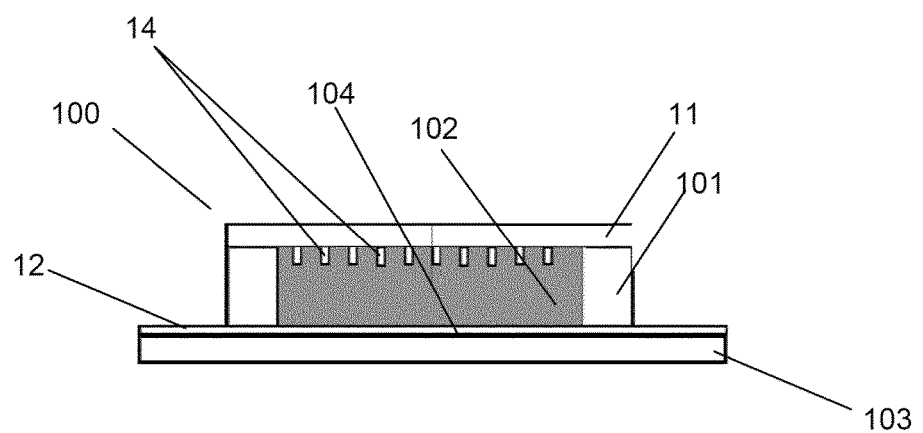
FIG. 4 shows a schematic view of a device according to the invention.

FIG. 4 shows a side view of another embodiment according to the invention. Here, the first electrode 11 from FIG. 3 has a region that comprises indentations, spikes or jags 14 that point toward the inside 102 of the reaction chamber 100.

Figure 5:
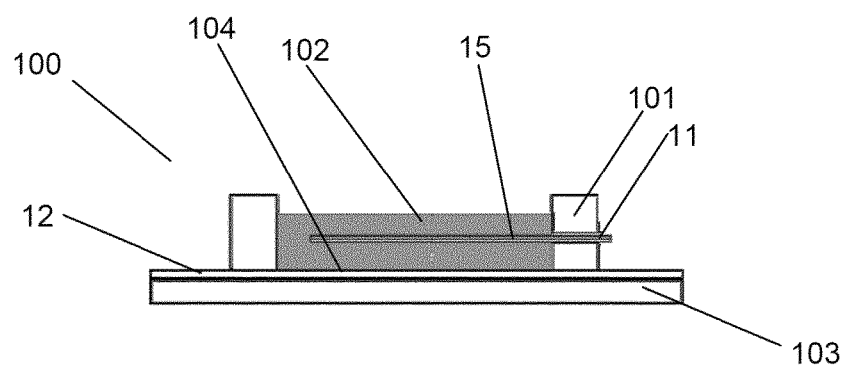
FIG. 5 shows a schematic view of a device according to the invention.
Figure 5:
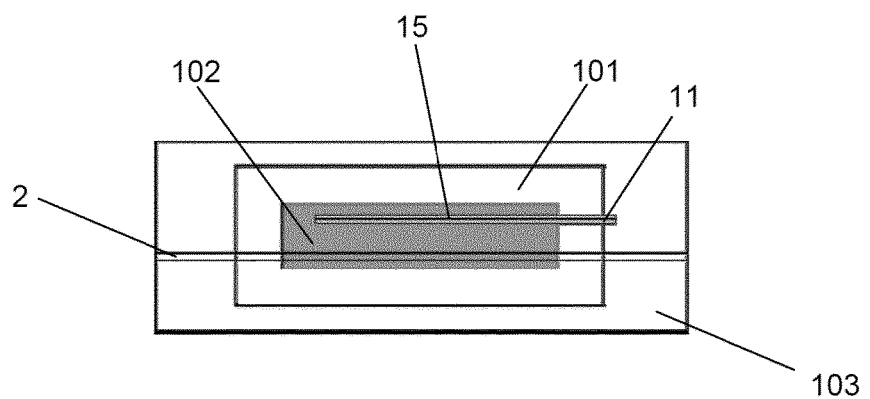

FIG. 5 shows another embodiment according to the invention. The upper panel shows a side view of the device according to the invention and the lower panel shows a top view of the device according to the invention.

In FIG. 5 the first electrode 11 is hollow and is particularly designed for the use as a microfluidic device. It preferably comprises a microfluidic channel 15 that extends along the inside of such a needle-shaped electrode 11. The first electrode 11 preferably penetrates the chamber wall 101 only on one side and extends towards the inside 102 of the reaction chamber 100 parallel to the second electrode 12. The microfluidic channel 15 is designed such that fluids can be delivered to the reaction chamber 100.

Figure 6:
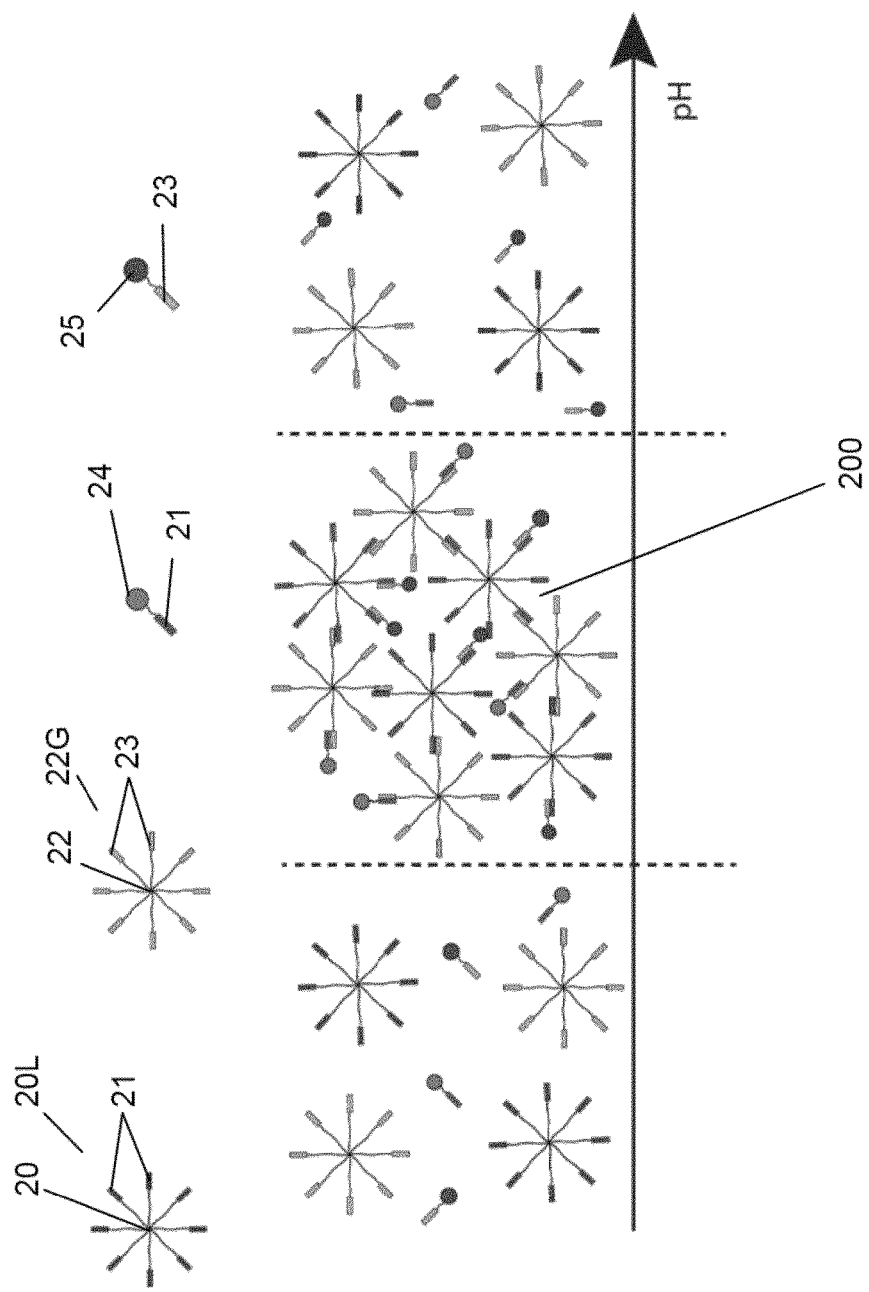
FIG. 6 shows a schematic illustration of the pH-dependency of a cross-linking reaction.
Figure 18:
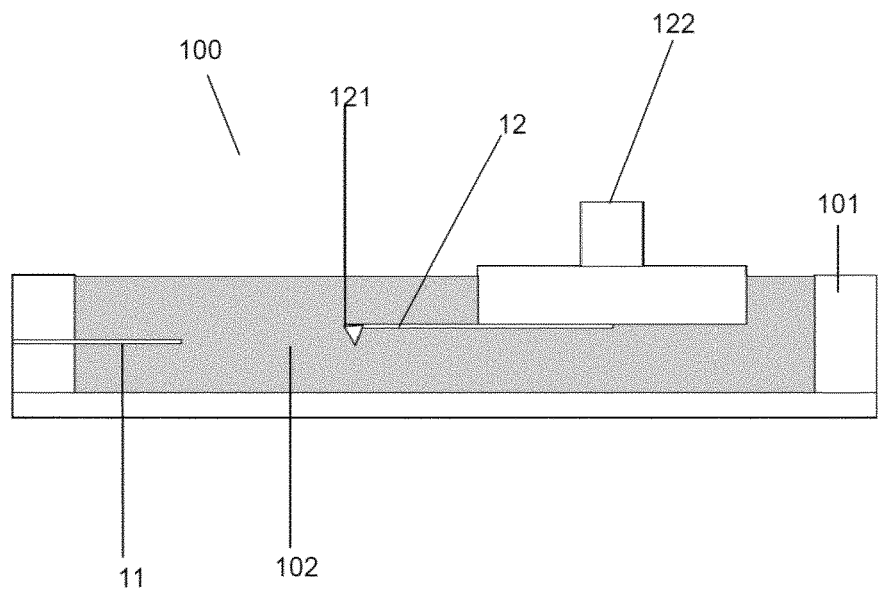
FIG. 18 shows a schematic view of a device according to the invention.

FIG. 18 shows the reaction chamber 100 comprising a first (counter-) electrode 11 that is arranged at the wall 101 of the reaction chamber 100 and particularly protrudes into the interior 102 (also denoted as inside herein) of the reaction chamber 100. The second (working-) electrode 12 is designed as a conductive scanning probe, particularly as an electrochemical atomic force microscope probe or a glass micro-electrode, particularly comprising a scanning tip 121 that is designed such that an applied voltage to said scanning probe will yield the largest change of pH of a solution in said reaction chamber 100 in proximity of the tip 121 of the scanning probe or second electrode 12. Said second electrode 12 is particularly three-dimensionally (x,y,z direction) movable within the reaction chamber 100, particularly by means of a controllable scanning stage 122. This embodiment of the device according to the invention particularly enables the production of fine hydrogel structures, such as wire or wire-like structures as the linking reaction is confined to a close proximity of the tip 121 of the second electrode 12. FIG. 6 shows a first compound comprising a first moiety 20, in this case a branched PEG molecule 20 functionalized with preferably a plurality of lysins 21 (Lys-PEG 20L), a second compound 22 comprising a second moiety 23, in this case also a branched PEG molecule 22 functionalized preferably a plurality of glutamines 23 (Gln-PEG 22G), and a third compound, in this case biomolecules 24, 25 functionalized with either lysine 21 or glutamine 23 (Lys-biomolecule 24L, Gln-biomolecule 25G). Lys-PEG 20L and Gln-PEG 22G are called precursors for the hydrogel 200.

Said precursors and the third compound 24L, 25G can be mixed with a transglutaminase, that is preferably an activated Factor XIII transglutaminase (FXIIIa) enzyme (EC 2.3.2.13, UniProt Nr: P00488) that catalyzes the formation of a covalent bond between a free amine group, particularly from a Lysine (Lys) 21 and an amide, particularly from a glutamine (Gln) 23. Such a reaction is classified as a Factor-XIII-mediated transglutamination.

Furthermore such a reaction is pH-dependent as the enzymatic activity of the FXIIIa depends inter alia on the pH of the solution. The activity of FXIIIa is highest at pH 8, where the FXIIIa works most efficient while at more acidic or basic conditions the efficiency is reduced (FIG. 6) [3]. In FIG. 6 a hydrogel 200 forms only in a certain pH window where the activity of the FXIIIa is sufficiently high to conduct such a cross-linking reaction between the Gln-PEG 22G and Lys-PEG 20L.

Figure 7:
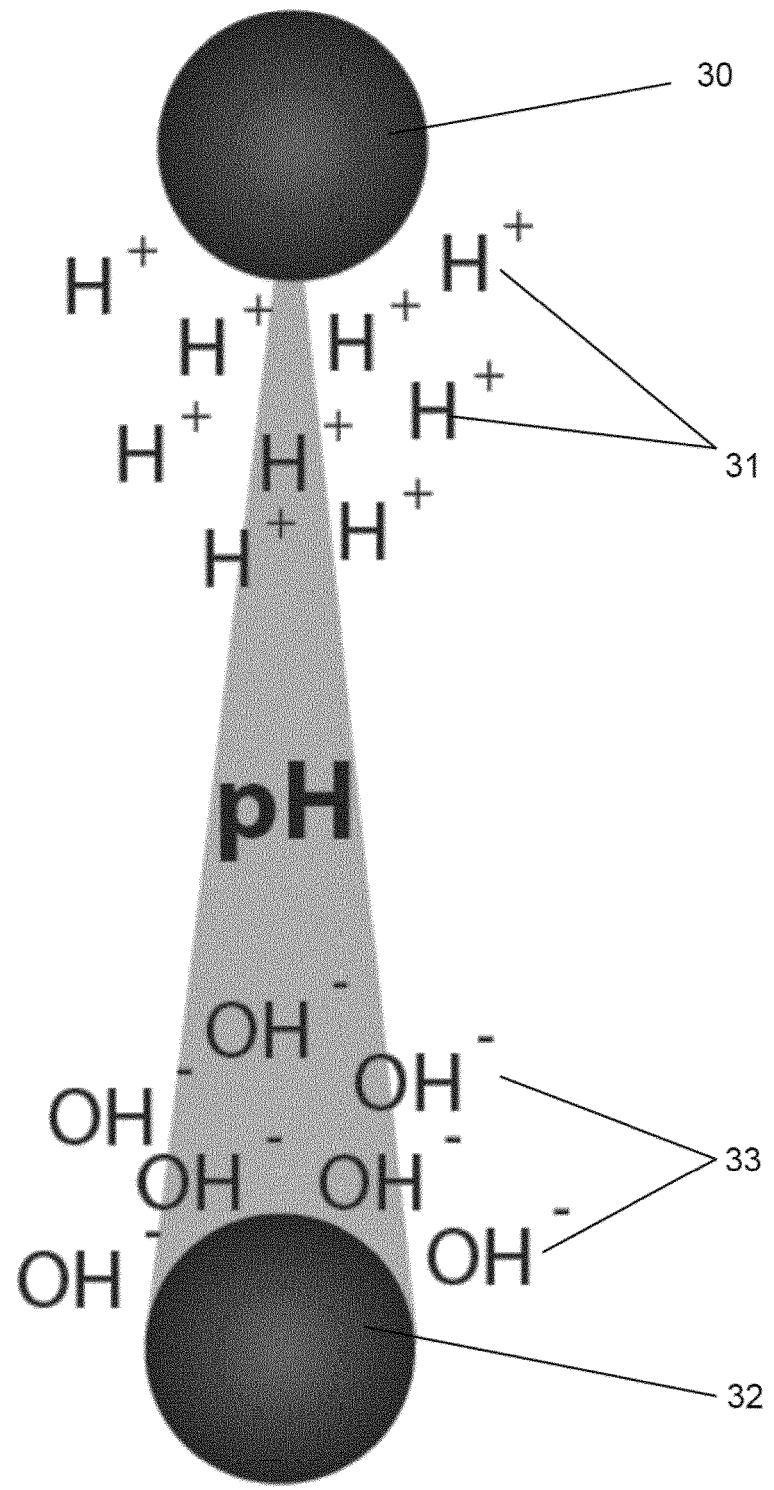
FIG. 7 shows a schematic illustration of the local pH distribution during electrolysis.

While in FIG. 6 the pH dependence of an enzymatically catalysed cross-linking reaction is depicted, FIG. 7 depicts schematically the pH change occurring at the electrode interface upon electrolysis of the solution [19]. The pH at the anode 30 decreases as more protons 31 are accumulating in the proximity of the anode 30 and the pH increases at the cathode 32 as more hydroxy-ions 33 accumulate near the cathode 32. In example 7 the production of Lys-PEG 20L and Gln-PEG 22G precursor is described in detail.

Example 1: Formation of a Hydrogel Under Different Conditions

A local change of pH of the solution as described in FIG. 6 can be achieved by the application of an electric current to the solution, via electrodes 11, 12, 13 (as described above), inducing electrolysis of the solution.

Such a voltage-induced electrolysis results in a local pH decrease at the anodic electrode-solution interface and in a local pH increase at the cathodic-buffer interface as shown in FIG. 7.

The extent of the region around each electrode 11, 12, 13 where a linking/cross-linking/polymerization of the precursors can be inhibited, confined or promoted, depends on the applied current density, pH and buffer capacity of the precursor solution in proximity of an electrode 11, 12, 13.

What kind of chemical reaction (polymerization, condensation reaction, cross-linking etc.) is taking place inter alia depends on the precursors used. In the case of Lys-PEG 20L, Gln-PEG 22G, it is particularly a cross-linking reaction.

To demonstrate that the formation of a hydrogel 200 is inhibited at the anode 30, particularly due to the local reduction of pH, FITC-tagged Lys substrate (Lys-FITC) is admixed to the solution comprising precursors and the FXIIIa. The solution in the present embodiment is a TRIS-buffer having a pH of 7.6.

Figure 8:
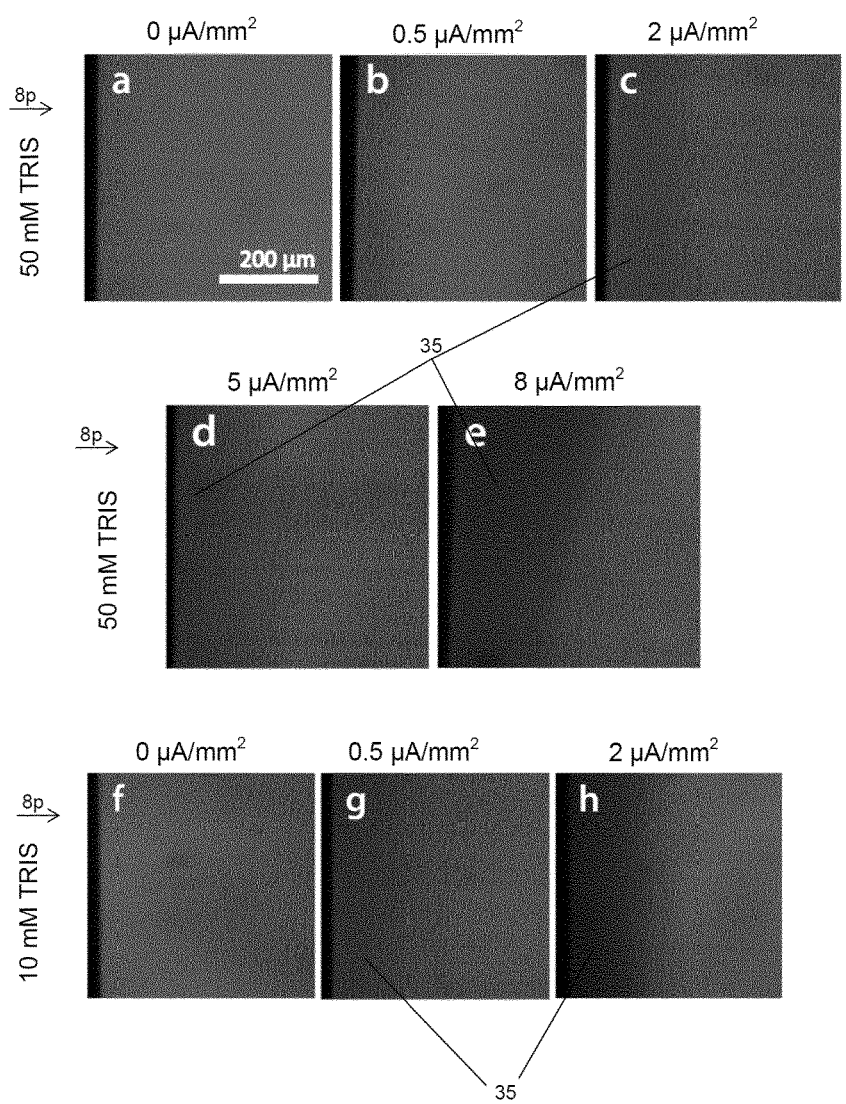
FIG. 8 shows microscope images of an example of a hydrogel according to the invention.
Figure 9:
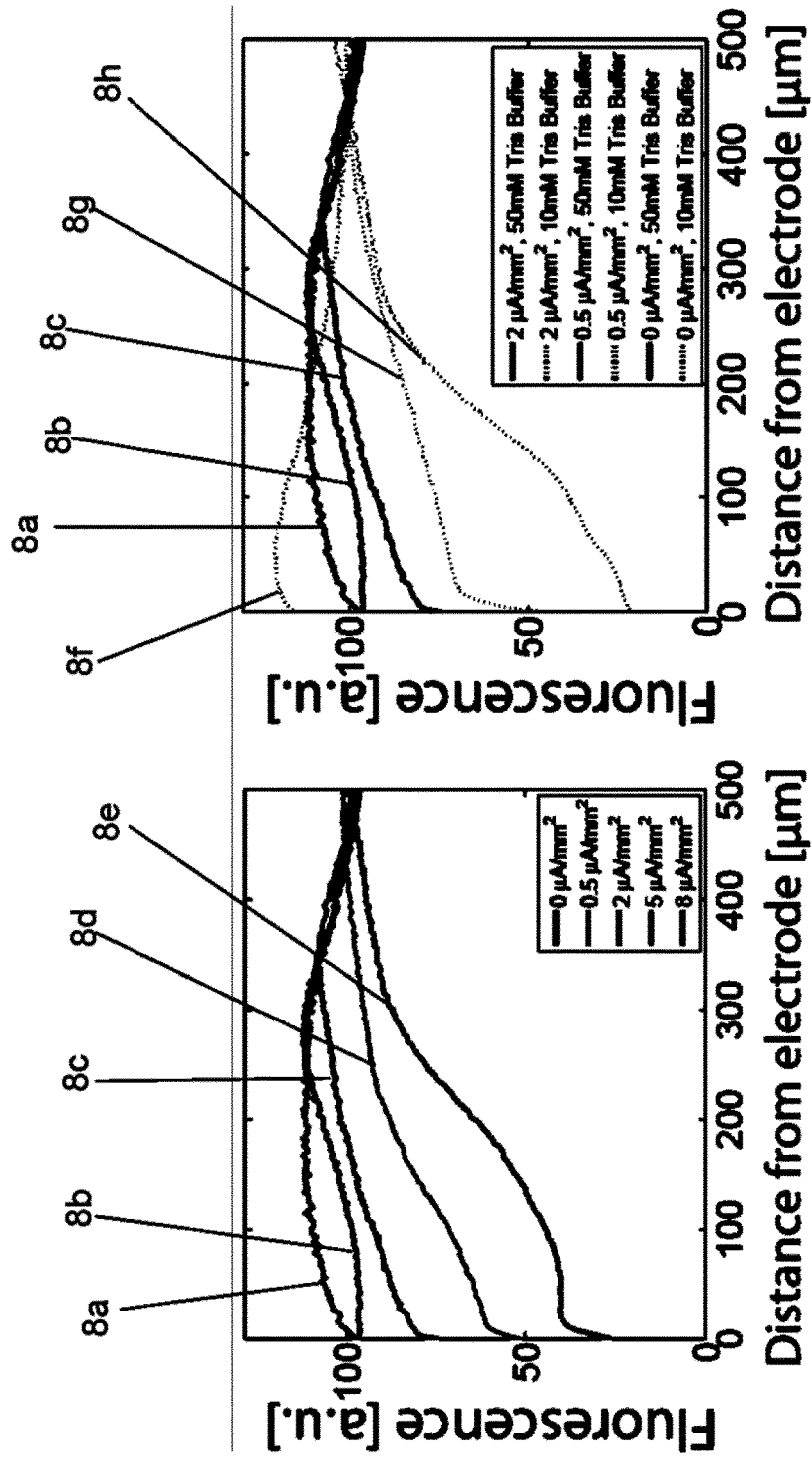
FIG. 9 shows quantitative graphs of derived of FIG. 8.

Confocal fluorescence microscopy images of carefully washed hydrogels 200 demonstrate that the hydrogel 200 formation is inhibited in proximity of the anode 30 as indicated by the reduced fluorescence intensity (brighter gray values indicate a higher fluorescence intensity). The extent of the inhibition region 35 around the anode 30 increased with an increasing current density and with a decreasing buffer concentration (FIG. 8 and FIG. 9). Example 10 describes the use of CLSM in more detail.

For the experiment depicted in FIG. 8, a solution (particularly comprising precursors and FXIIIa and Lys-FITC) is casted in the reaction chamber 100 that comprises two electrodes 11, 12. The electrodes are preferably Tungsten-wires. The anode 30 is placed on the left from each microscope image and the cathode 32 is located right from the respective microscope image.

FIG. 8 $a$-$e$ shows confocal fluorescence images of the FITC-tagged hydrogels 200 prepared with a Tris concentration of 50 mM wherein the current density was adjusted between 0 and 8 $\mu A/mm^2$ (FIG. 8 $a$: 0 $\mu A/mm^2$, FIG. 8 $b$: 0.5 $\mu A/mm^2$, FIG. 8 $c$: 2 $\mu A/mm^2$, FIG. 8 $d$: 5 $\mu A/mm^2$ and FIG. 8 $e$ 8 $\mu A/mm^2$).

FIG. 8 $f$-$h$ shows images of hydrogels prepared with a Tris concentration of 10 mM and increasing current densities adjusted between 0 and 2 µA/mm² (FIG. 8 f: 0 µA/mm², FIG. 8 g: 0.5 µA/mm², FIG. 8 8 h: 2 µA/mm²).

A quantification of the measured fluorescence intensities along the direction indicated by 8p is presented in FIG. 9.

In particular, at 50 mM Tris buffer a decrease in fluorescence intensity in proximity of the anode 30 is not observed when a current density of 0.5 µA/mm² is applied to the solution (FIG. 8 b).

In contrast, a decrease in fluorescence is already visible at 0.5 µA/mm² when the Tris concentration is 10 mM (FIG. 8 g).

At a concentration of 50 mM Tris the formation of the hydrogel is inhibited up to a distance of approximately 200 µm away from the anode 30 for a current density of 8 µA/mm² (FIG. 8 e). The inhibition region is about the same size for 2 µA/mm² if the Tris concentration is 10 mM (FIG. 8 h). In example 8 and example 9 more details about the hydrogel production are described.

Example 2: Cross-Linking in Proximity of an Electrode

Another embodiment of the invention is realized by preparing solutions containing the precursors, FXIIIa and fluorescence marker (Lys-FITC) as described above but at pH 5 and pH 11 respectively. Under both pH conditions the precursors will not be cross-linked when no electric current is applied to the solution (FIG. 10 a and FIG. 10 d), as the FXIIIa activity is inhibited.

Figure 10:
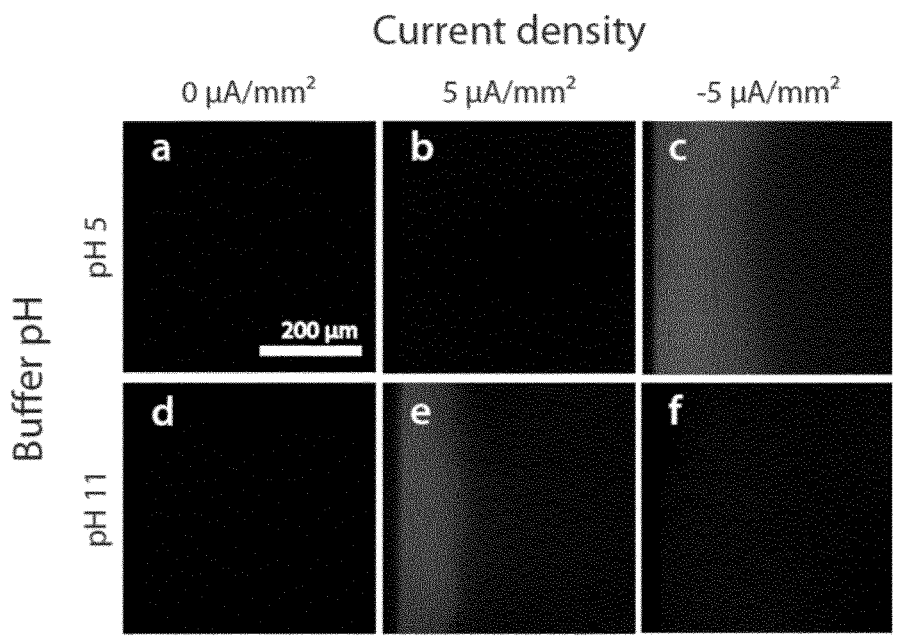
FIG. 10 shows microscope images of an example of a hydrogel according to the invention.

However, when an electric current density of −5 µA/mm² is applied to such a solution the formation of the hydrogel takes place in proximity of the cathode for the hydrogel 200 prepared at pH 5 (FIG. 10 c, cathode placed on the left side of the image) and in proximity of the anode (+5 µA/mm²) for the hydrogel prepared at pH 11 (FIG. 10 e, anode placed on the left side of the microscope image). The cross-linked regions extend from approximately 100 µm to 200 µm at the anode (for pH 11, FIG. 10 e) and at the cathode (for pH 5, FIG. 10 b), respectively.

In this embodiment the choice of the solutions' pH is made to be symmetrically distant from the optimum enzymatic activity pH of the FXIIIa.

It is assumed that the cross-linking region extends equally from the anode 30 and from the cathode 32. However, it has not been checked whether the enzymatic activity of FXIIIa decreases symmetrically at acidic and basic pH.

The inhibition of the cross-linking reaction observed in FIG. 8 and FIG. 9 is caused neither due to a quenching effect of the FITC caused by the electric current and/or pH change nor due to electrophoretic mobility of molecules but to the control of the enzymatic activity of FXIIIa by spatially altering the pH of the solution.

According to the invention the formation of a hydrogel 200 can thus be confined particularly in proximity of an electrode. The FXIIIa activity can be actively controlled, particularly inhibited or activated by electrochemical modulation of the local pH of the solution.

Example 3: Removal of Electrodes from the Hydrogel Manufactured According to the Invention and Assessment of the Mechanical Stress on Hydrogels Upon Tungsten Electrode Removal In another example of an embodiment according to the invention the ability to spatially control the formation of a hydrogel 200 using Lys-PEG 20L and Gln-PEG 22G as precursors can be used to create spatially defined biological microenvironments. Hydrogels 200 produced using particularly Lys-PEG 20L, Gln-PEG 22G and particularly Lys- or Gln-labeled biomolecules 24L, 25G or markers will be referred to TG-PEG (transglutamination-mediated PEG). The formation of particularly micro-channels in three-dimensional hydrogels 200 is a challenge in the development of in vitro scaffolds. Chrobak and colleagues addressed this challenge by placing a stainless steel microneedle prior to a gel polymerization and by subsequently removing said needle to form a micro-channel [20, 21]. Such an conventional approach where hydrogel formation takes place without applying a voltage to the solution of precursors and enzyme, and using particularly metal wires as templates to create micro-channels in such (unstructured) PEG-hydrogels often results in the disruption of the micro-channels and the hydrogel because of the too strong adhesion of the hydrogel to the wire surface.

In contrast to the conventional approach, applying the method according to the invention using tungsten wires as anodic-electrodes 30 formation of the TG-PEG hydrogel 200 can be inhibited in a confined region around said tungsten wires using appropriate conditions for pH, current density etc. as for example described in Example 1 and 2.

As a result of the local inhibition of the cross-linking at the anode's 30 interface, channels can be created extending through the hydrogel along the electrode wire, without mechanically stressing the hydrogel, when said wire is removed after cross-linking of the hydrogel is complete.

The mechanical stress induced to the hydrogel during the Tungsten wire removal is quantified by suspending 20 µm fluorescent micro-particles in the hydrogel precursor solution.

Figure 11:
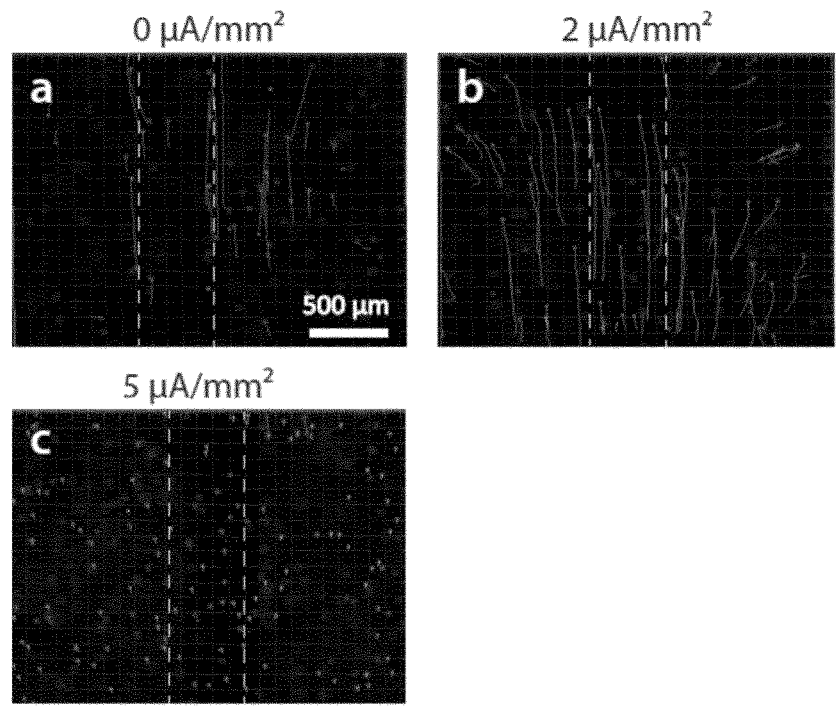
FIG. 11 shows microscope images and quantification of hydrogel displacement upon electrode removal.
Figure 11:
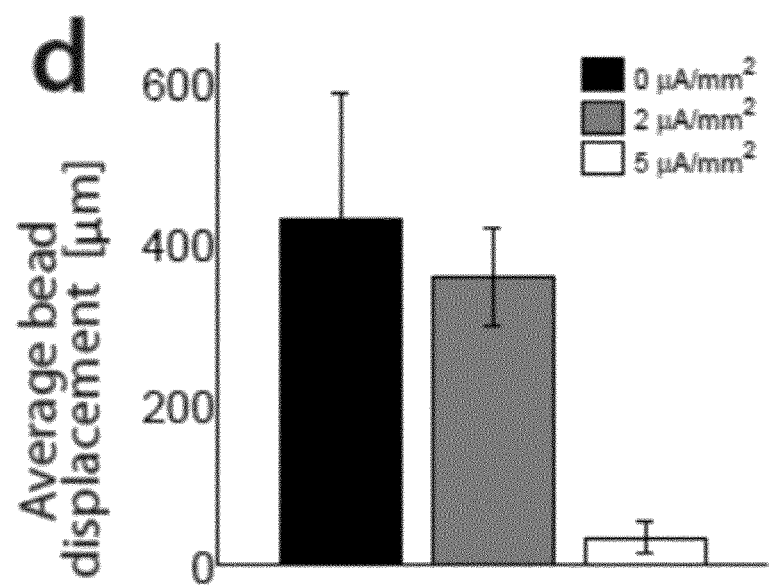

FIG. 11 displays micro-particle displacement caused by removal of the electrode for different current densities. In the microscopic images (FIG. 11 a-c) the micro-particles after removal of the electrode can be seen as gray dots and the displacement from the position before removal of the electrode is indicated by gray lines ending at the gray dots. The white dashed lines indicate the position of the electrode. FIG. 11 shows the average displacement of the micro-particles after removal of the electrode for FIG. 11 a-c (The black bar: corresponds to FIG. 11 a, the gray bar corresponds to FIG. 11 b and the white boxed bar corresponds to FIG. 11 c).

By tracking the micro-particle displacement as a function of the applied current density (FIG. 11 d), it is found that an current density of 0 µA/mm² (FIG. 11 a) or 2 µA/mm² (FIG. 11 b) is insufficient whereas a current density of 5 µA/mm² (FIG. 11 c) is sufficient to suppress bead displacement (as the gray lines ending in the gray dots are shortest or non-existent) and thus, the consequent prevention of damage to the hydrogel structure. FIG. 11 d shows the displacement of particles that are tracked upon removal of the Tungsten needle/wire (dashed lines) from TG-PEG hydrogels polymerized with various anodic currents: 0, 2 and 5 µA/mm2 (a, b and c). d) Quantification of bead displacement (mean SD, n=3).

Figure 12:
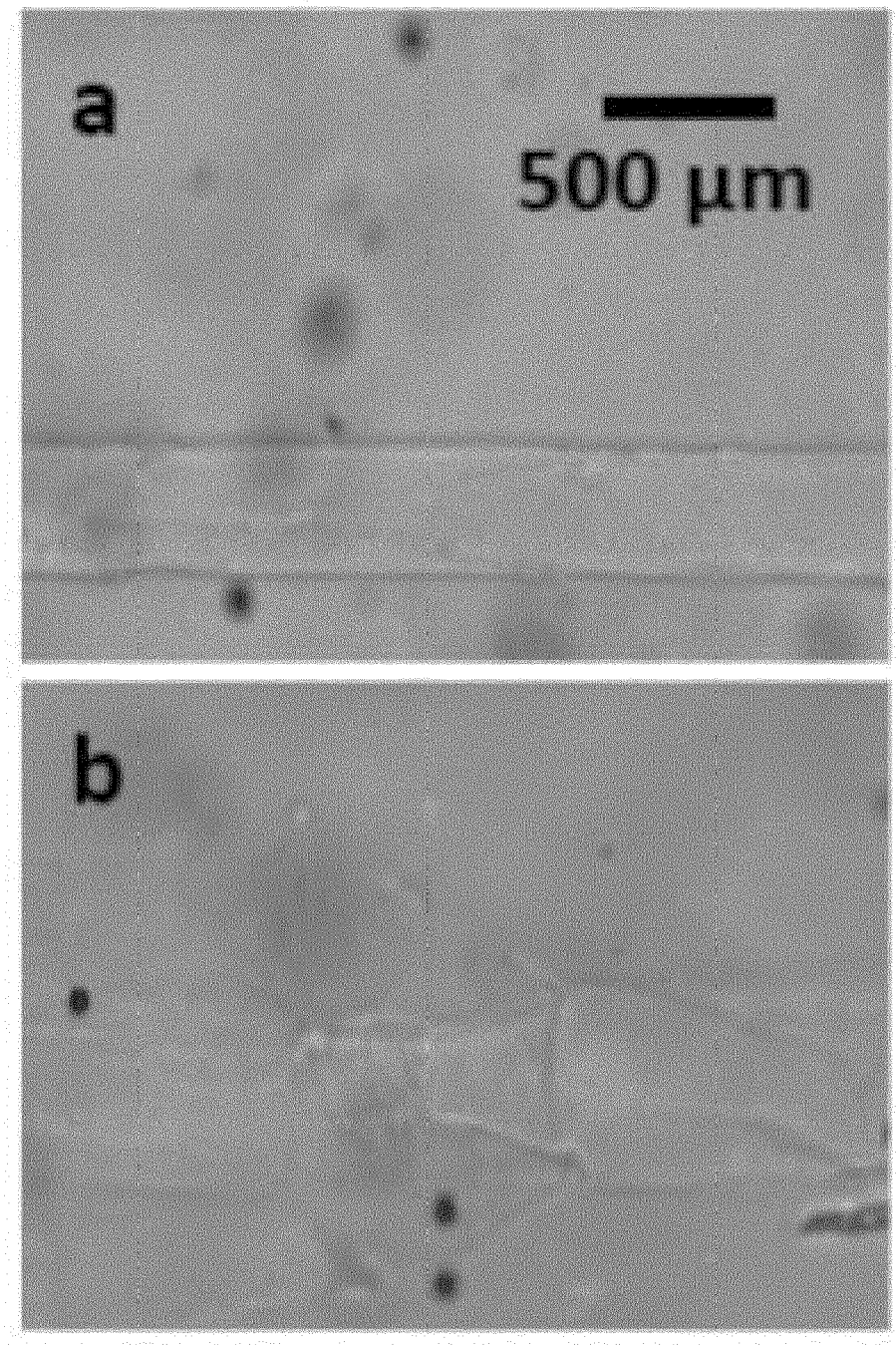
FIG. 12 shows brightfield microscope images of microchannel fabrication according to the invention and conventional approach.

FIG. 12 depicts brightfield microscope images from a TG-PEG hydrogel 200 formed at 0 µA/mm² (FIG. 12 a,b). It can be seen that in FIG. 12a the micro-channel left by the removed electrode is intact whereas the micro-channel in FIG. 12b is disrupted after removal of the electrode. Example 11 describes in more detail how the displacement of the hydrogel can be quantified.

Figure 13:
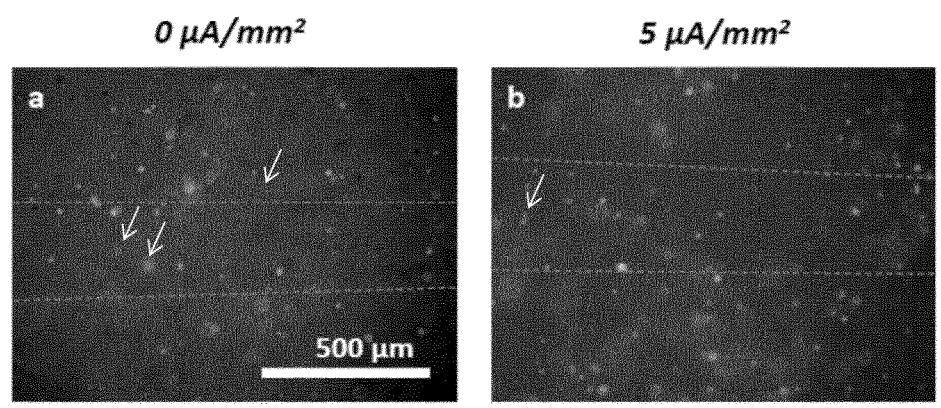
FIG. 13 shows live/dead cell assay microscope image.

Example 4: Live/Dead Assay on Mesenchymal Stem Cells Suspended in the Hydrogel During Hydrogel and Micro-Channel Manufacturing The production of micro-channels can be even performed in the presence of cells without affecting their viability. FIG. 13 shows a Live/Dead assay on mesenchymal stem cells (MSCs) suspended in the hydrogel 200 during channel production with 0 (FIG. 13 a) and 5 µA/mm2 (FIG. 13 b). No difference in cell viability was observed, as almost no dead cells (white arrows) visible. For the Live/Dead assay, $10^6$/mL human bone marrow derived MSCs are re-suspended in TG-PEG precursor solution. The solution is cross-linked with (FIG. 13 b) and without (FIG. 13 a) anodic polarization prior to electrode (Tungsten-wire) removal. The Live/Dead assay (Sigma Aldrich, Switzerland) is carried out according to the manufacturer's protocol. Said assay is based on a fluorescent marker that emits in the red spectral region for dead cells and emits in the green spectral region for live cells.

Example 5: Electrochemical Control of Hydrogel Cross-Linking can be Used for Creating Complex-Structured 3D Microenvironments that are Locally Functionalized In this example it is demonstrated that a microenvironment made from TG-PEG can be a hydrogel 200 comprising several proteins, peptides and other biomolecules 24, 25 that support the viability of biological entities, such as e.g. cells. Microenvironments that are particularly hydrogels 200 characterized by a defined architecture and by a controlled spatial distribution of chemical moieties, such as biomolecules 24, 25, that can be used to instruct cells in culture can serve as provisional cell-permissive matrices, which provide graded biological cues, much like natural extra-cellular matrices (ECMs), are of great importance.

FIGS. 14 to 17 show an example of the electrochemical control according to the invention of a hydrogel 200 that cross-linking can be used for the production of complex-structured 3D microenvironments (TG-PEG) that are locally functionalized with biological signals. In this embodiment of the invention a two-component biocompatible microenvironment is manufactured.

Figure 14:
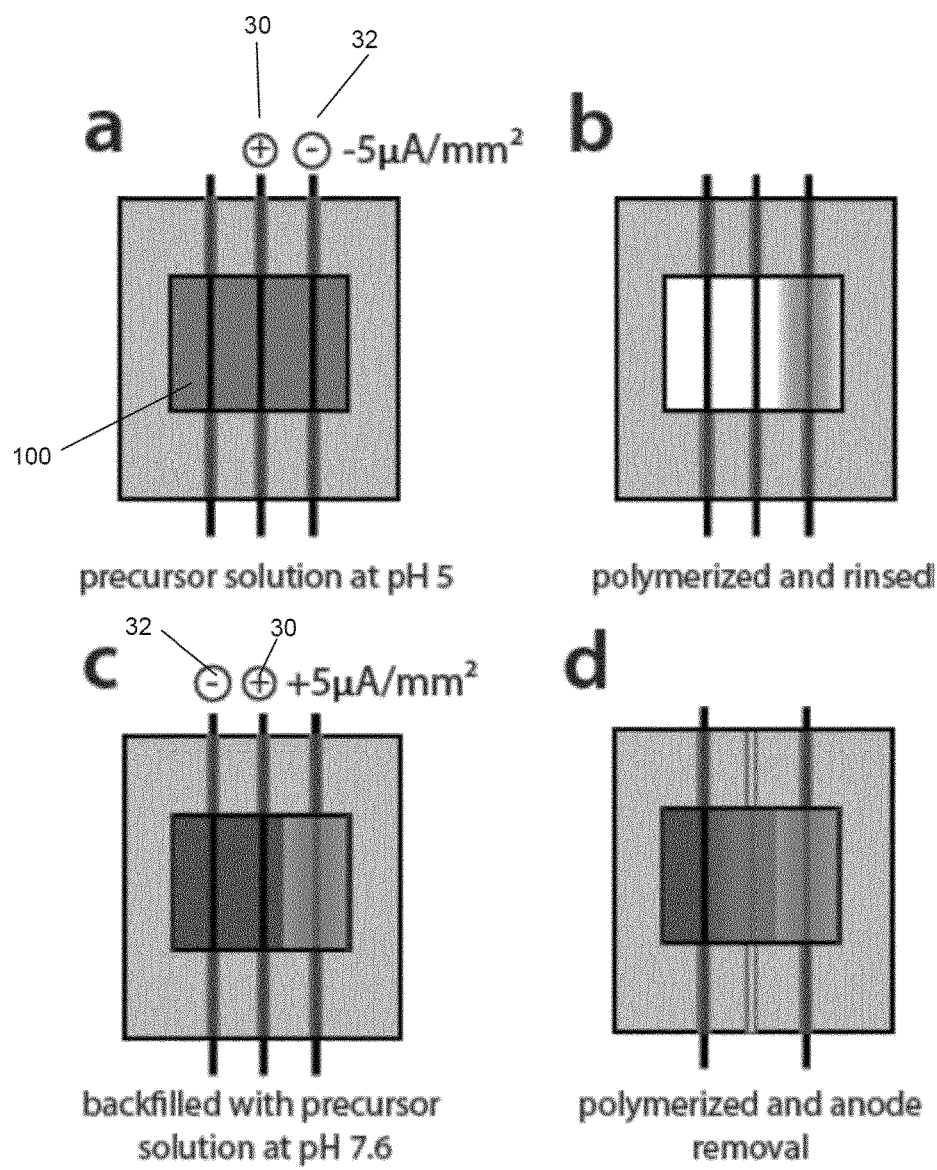
FIG. 14 shows a schematic of a structured 3D two-component hydrogel production according to the invention.
Figure 15:
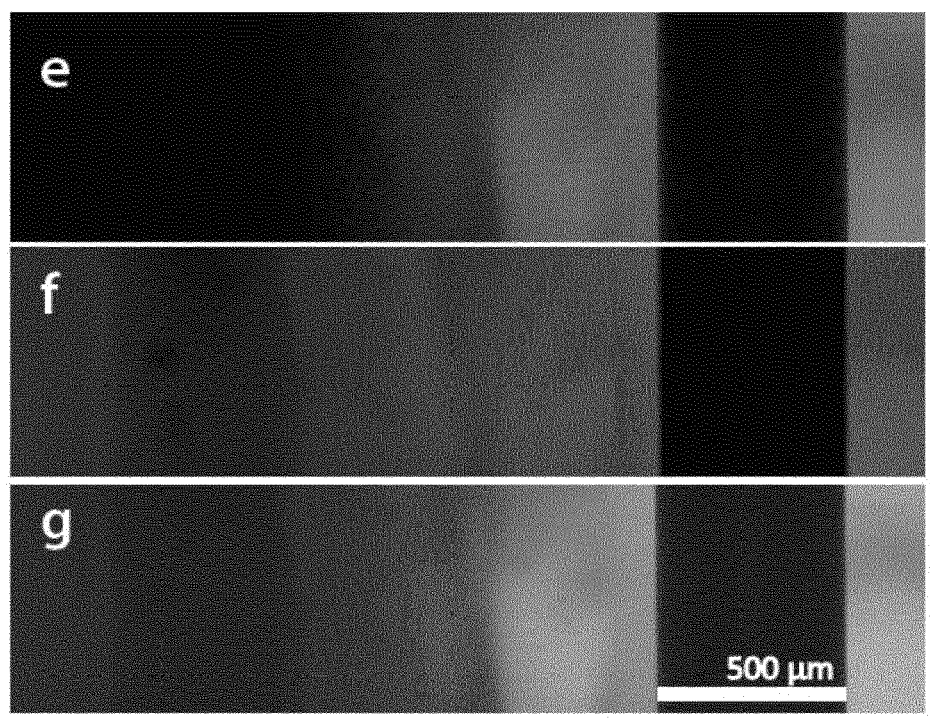
FIG. 15 shows microscope images of a structured 3D two-component hydrogel according to the invention.
Figure 16:
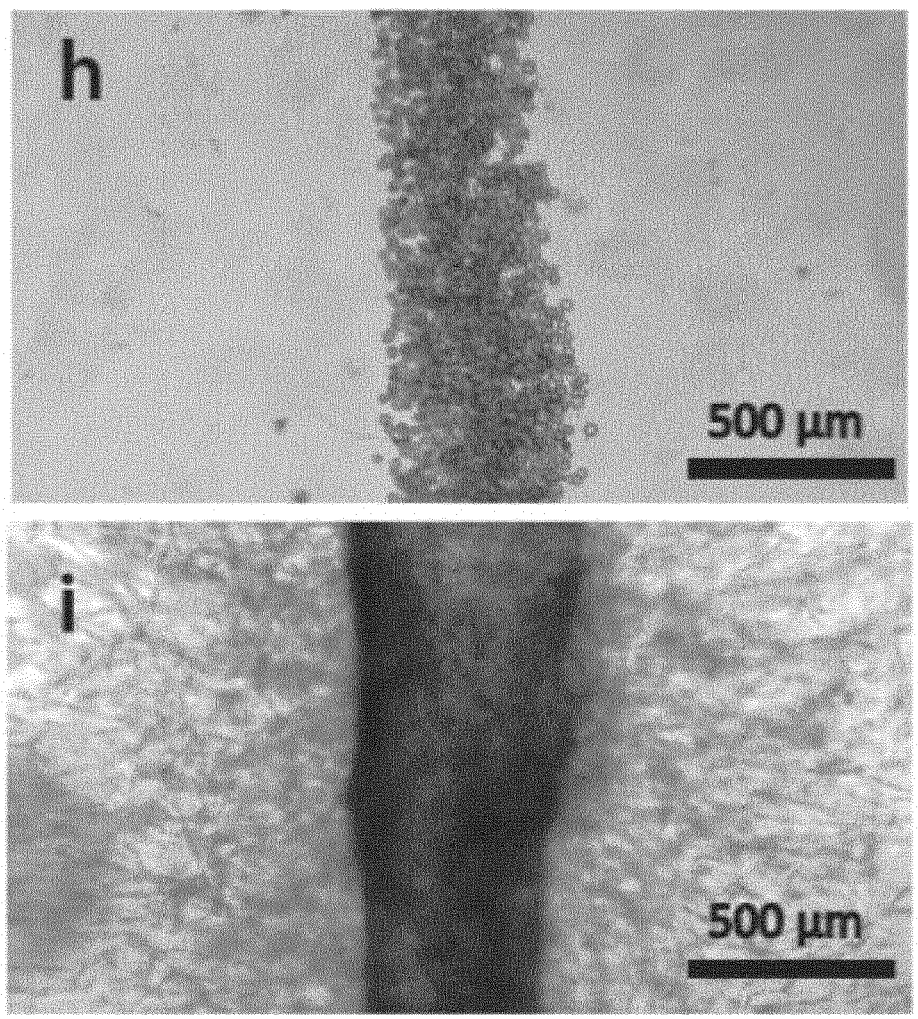
FIG. 16 shows a cell invasion assay co-manufactured with a hydrogel according to the invention.
Figure 17:
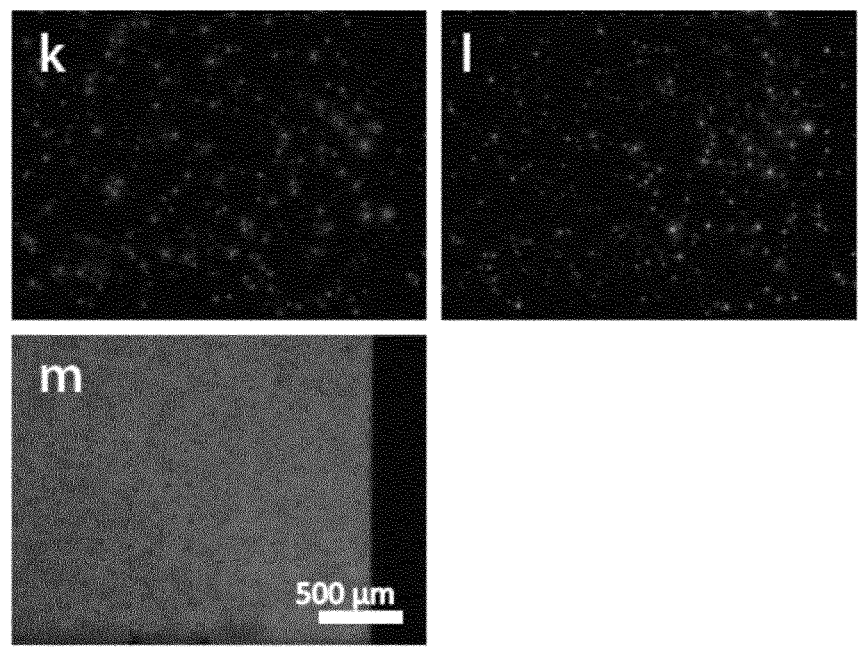
FIG. 17 shows cell distribution in a two-component hydrogel.
Figure 17:
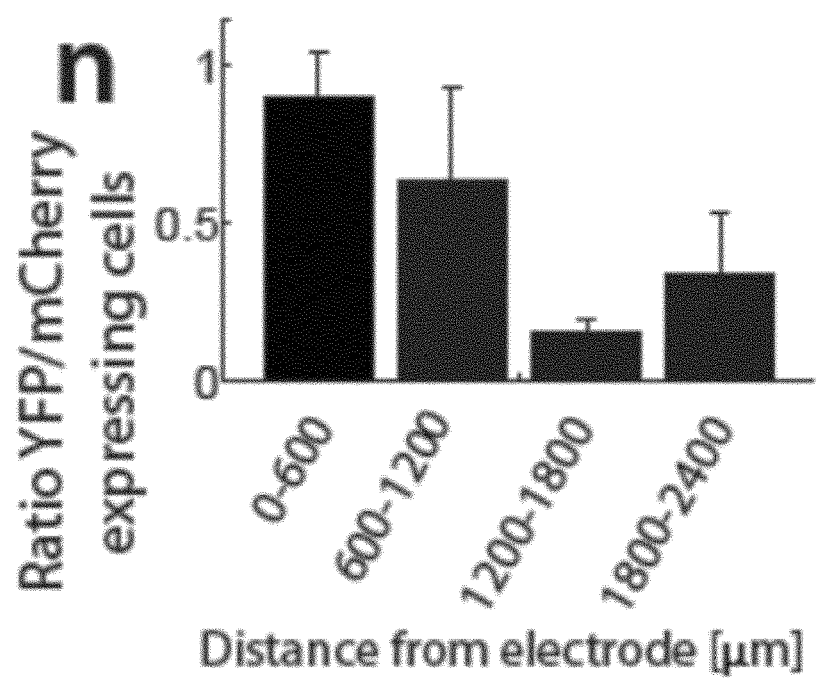

FIG. 14 a-d) shows a simplified schemes depicting the production of an engineered microenvironment: FITC and IL-4 (interleukine-4) containing hydrogel precursors at pH 5 are cast in a PDMS reaction chamber and locally cross-linked around a cathode applying −5 µA/mm2. After cross-linking and removal of the unbound precursors by rinsing (FIG. 14 b), a second hydrogel precursor solution functionalized with Alexa 561 (pH 7.6) is poured in the reaction chamber and an anodic current of 5 µA/mm2 is applied to a third electrode during cross-linking (FIG. 14 c), resulting in a TG-PEG microenvironment constituted, after electrode removal, of a channel for cell delivery and a locally biofunctionalized region (FIG. 14 d). Confocal microscopic images of the resulting microenvironment (FIG. 15 g) with FITC-incorporated region (15 e) and a channel formed in the Alexa 561 gel (FIG. 15 f). MSCs were perfused in the channel (FIG. 16 h) and invaded the surrounding environment (FIG. 16 i, picture taken at day 7). IL4-sensing HEK cells, constitutively expressing mCherry (FIG. 17 k), expresses higher YFP levels (FIG. 17 l) in proximity of the IL-4-incorporating gel. A Bright field image is shown to locate the electrode (FIG. 17 m). FIG. 17 n: Ratio (y-axis) of YFP/mCherry expressing cells as function of the distance (x-axis) from the electrode (values represent means and standard deviation of 3 experiments). Example 13 describes in more detail how the IL-4 response assay can be performed.

In the following the experiment of the present example is described in more detail: A hydrogel 200 according to the invention is sequentially produced: In a first step a cross-linking reaction of a pH 5 precursor solution comprising also FITC and IL-4 functionalized to be convertible by FXIIIa is poured in the reaction chamber 100. A TG-PEG hydrogel 200 forms around the cathode 32 by applying −5 µA/mm$^2$ (FIG. 14 a). After thorough washing of the unbound hydrogel precursors and chemical compounds (schematically shown in FIG. 14 b) the PDMS reaction chamber 100 is backfilled with another Alexa 561-Gln-labelled TG-PEG hydrogel precursor solution (pH 7.6) (FIG. 14 c), in which a channel is created as particularly described according to example 3 above (FIG. 14 d). Alexa561 is a fluorescent dye emitting at a different (red-shifted) wavelength than FITC. Various cell types ranging from bone marrow derived MSCs, preosteoblasts or fibroblasts (not shown) can be delivered to the channel and invade the surrounding environment, that for example contains biomolecules 24, 25 incorporated, particularly growth factors (FIG. 16 i). Additionally, HEK cells engineered to sense and report IL-4 by expressing a YFP (yellow fluorescent protein) signal, and placed in a microenvironment containing a local IL-4 repository, respond in a spatial specific manner (FIG. 17 k-n). In particular, the number of IL-4 sensitive cells expressing high levels of YFP (FIG. 17 l) over the number of transfected cells (mCherry positive cells, FIG. 17 k), increase at the vicinity of the IL-4-incorporated gel (FIG. 17 m+n).

Taken together, the ability of cells to invade hydrogels 200 that are produced according to the invention and to sense the locally immobilized molecular cues demonstrated the potential of this approach to generate 3D structured substrates (3D structured hydrogels) emulating the ECM-mediated presentation of growth factor or cytokine gradients.

Example 6: Preparing a Reaction Chamber with Wire-Electrodes According to the Invention Preparation of the PDMS reaction chamber 100. Polydimethylsiloxane (PDMS) reaction chambers 200 are made as follows: the silicon elastomer and the curing agent (Sylgard 184, Dow Corning Corporation, USA) are mixed (10:1 in mass) at 2000 rpm for 3 min in a ARE-250 mixer (Thinky Corporation, Japan). The mixture is subsequently poured into poly(methyl methacrylate) (PMMA) moulds, where 500 µm in diameter stainless steel wires are positioned to create admission holes 105, 106 in the wall 101 of the chamber 100 for the electrodes 11, 12, 13. The mixture is subsequently degassed for 30 min in a vacuum chamber and baked for 4 h at 60° C. The stainless steel wires and the PDMS reaction chamber 100 are removed from the PMMA moulds, rinsed with isopropanol (IPA), oxygen plasma cleaned (1 min at 300 W, Plasma-System 100, Technics Plasma GmbH, Germany) and finally pressed onto microscope glass cover slips 103. Straightened Tungsten wires 11, 12, 13 (W, 500 µm in diameter, Advent Research Materials Ltd, UK) are inserted in the PDMS reaction chamber 100 and connected to a potentio-galvanostat in a two electrode setup (PGU-10V-1A-IMP-S and ECMwin computer interface, Elektroniklabor Peter Schrems, Germany).

Example 7: Production of Lys-/Gln-Peg Precursors According to the Invention

Eight-arm PEG 20, 22 precursors containing the pending Factor XIII activated (FXIIIa) substrate peptides glutamine acceptor substrate (n-PEG-Gln) or lysine donor substrate containing a MMP-sensitive linker (n-PEG-MMP-sensitive-Lys) are produced and characterized as described elsewhere [4]. In brief, eight-arm PEG mol. wt. 40000 is purchased from Nektar (Huntsville, Ala., USA). Divinyl sulfone is purchased from Aldrich (Buchs, Switzerland). PEG vinylsulfone (PEG-VS) is produced and characterized as described elsewhere [22]. The FXIIIa substrate peptides H-NQEQVSPL-ERCG-NH2 (TG-Gln) Ac-FKGG-GPQGI-WGQ-ERCG-NH2 (MMP-sensitive-Lys), and the adhesion ligand Ac-GCYGRDGSPG-NH2 (TG-Gln-RGD) are obtained from NeoMPS (Strasbourg, France) (immunograde, C18-purified, HPLC analysis: >90%). The NQEQVSPL cassette corresponds to the FXIIIa substrate site in α2-plasmin inhibitor [23], the FKGG cassette to an optimized FXIIIa substrate site [24], and the ERCG cassette to the vinylsulfone-reactive Cysteine [25]. In separate vials TG-Gln, TG-MMP-sensitive-Lys are added to PEG-VS in 1.2-fold molar excess over VS groups and allowed to react in 0.3 M triethanolamine (pH 8.0) at 37° C. for 2 h. The products are dialyzed (Snake Skin, MWCO 10K, PIERCE, Rockford, Ill., USA) against ultrapure water for 3 days at 4° C. After dialysis, the salt-free products (8-PEG-MMP-sensitive-Lys and 8-PEG-Gln, respectively) are lyophilized.

Example 8: TG-PEG Hydrogel Preparation 1 mL of FXIIIa (200 U/mL, Fibrogammin, CSL Behring, Switzerland) is activated with 100 µL of thrombin (20 U/mL, Sigma-Aldrich, Switzerland) for 30 min at 37° C. Small aliquots of activated FXIIIa can be stored at −80° C. for further use. Hydrogels with a final dry mass content of 1.5% are prepared by stoichiometrically balanced ([Lys]/[Gln]=1) precursor solutions of n-PEG-Gln and n-PEG-MMP-sensitive-Lys in Tris-Buffer (Tris) with varying molarity and pH (see above), containing 50 mM calcium chloride ($CaCl_2$).

Furthermore optionally Lys-FITC, TG-Alexa 561, Gln-RGD or combinations are added to the precursor solution prior to initiation of cross-linking by 10 U/mL thrombin-activated FXIIIa and vigorous mixing.

Example 9: Electrochemical Control of TG-PEG Cross-Linking According to the Invention To study the effect of electrochemistry on TG-PEG polymerization a 60 µL solution composed of TG-PEG, Tris (50 mM or 10 mM, pH 5, 7.6 or 11), $CaCl_2$ and a fluorescent agent such as for example Lys-FITC, TG-Alexa 561 or fluorescent polystyrene beads (Fluoresbrite Plain YG 20 micron microspheres, Polyscience Inc.) are mixed with the FXIIIa. The mixture has to immediately be poured in the PDMS reaction chamber. The cross-linking of the TG-PEG is allowed to progress during 6 minutes in presence of a DC current applied in galvanostatic mode. The current density can be varied in a range between 0 and 8 $\mu A/mm^2$.

Example 10: Confocal Laser Scanning Microscopy (CLSM)

The TG-PEG hydrogel-electrode interfaces are imaged using a LSM 510 confocal laser scanning microscope (Carl Zeiss AG, Germany). It might be necessary to adjust the focal plane to obtain the maximal section of the Tungsten wire (500 µm). The FITC is detected upon excitation at 490 nm with 0.7% laser power, and an emission band pass filter 505-550 nm. Alexa 561 can be detected upon excitation at 515 nm and with an emission band pass filter 575-615 nm. The intensity profiles can be obtained over a 500×500 µm field of view by setting the minimum intensity as the average intensity of the electrode and by normalizing the values over the average intensity of the distal 200 µm (maximal intensity). At least 3 samples per condition should be analyzed and 2 images per electrode are acquired.

Example 11: Quantification of Hydrogel Displacement Upon Electrode Removal

To study the effect of electrochemistry on the adhesion of the Tungsten wire 11, 12, 13 from the TG-PEG hydrogel 200 upon removal and on the subsequent formation of a microchannel, the displacement of 20 µm polystyrene particles dispersed in the hydrogel 200 is tracked using a Leica fluorescence microscope (BM550B, Leica Microsystems, Germany). The TG-PEG hydrogel 200 is prepared as described above and the Tungsten wires 11, 12, 13 are manually pulled out of the hydrogel 11, 12, 13. Images are recorded every 100 ms and the particles are detected upon excitation at 488 nm. The particle trajectories are calculated using an Image J script previously described [26].

Example 12: Cell Invasion Assay

After channel formation, a solution of 106/mL human bone marrow derived mesenchymal stem cells (MSCs) in serum free DMEM/F-12+GlutaMAX™ (Gibco Life Technologies, cat. no. 31331-028) supplemented with 1% (v/v) penicillin/streptomycin solution (P/S, Gibco Life Technologies, cat. no. 15140-122) is perfused into the channel. Hydrogels were subsequently placed in medium supplemented with human platelet-derived growth factor BB (PDGF-BB, 10 ng/ml, Peprotech, cat. no. 100-14B) and kept in culture for 7 days. Bright field images were acquired with a ZEISS Axiovert 200M inverted microscope.

Example 13: Cell IL-4 Response Assay

HEK-IL4 reporter cells are produced as described previously [6]. In brief, HEK 293T cells are transfected with pHW40 (PSTAT6-eYFP-pA) and the constitutive expression vector STAT6 (obtained from Open Biosystems, Huntsville, Ala., Clone ID 5530399). A constitutive mCherry expression plasmid (pMK47) is used as internal control. For the 3D IL4 response assay, 106/mL reporter cells are resuspended in TG-PEG precursor solution and cultured for 24 hours in DMEM/F-12+GlutaMAX™ supplemented with 10% (v/v) fetal calf serum (FCS, Gibco Life Technologies, cat. no. 10500) and 1% (v/v) P/S. Fluorescent and brightfield images are acquired with a LEICA DM16000 B inverted microscope.

As a measure of IL-4 responding cells, the ratio of cells expressing YFP over cells expressing mCherry might be determined with ImageJ. In particular, when a microenvironment is produced with a IL-4 functionalized area around an electrode, the IL-4 response in 600 µm wide regions is measured, and the mean and standard deviation calculated out of 3 independent experiments.

REFERENCES

[1] M. P. Lutolf, J. A. Hubbell, Nat Biotech 2005, 23, 47; N. Tirelli, M. P. Lutolf, A. Napoli, J. A. Hubbell, Reviews in Molecular Biotechnology 2002, 90, 3; M. V. Tsurkan, K. Chwalek, S. Prokoph, A. Zieris, K. R. Levental, U. Freudenberg, C. Werner, Advanced Materials 2013, 25, 2606.

[2] M. Ehrbar, A. Sala, P. Lienemann, A. Ranga, K. Mosiewicz, A. Bittermann, S. C. Rizzi, F. E. Weber, M. P. Lutolf, Biophysical Journal 2011, 100, 284.

[3] M. Ehrbar, S. C. Rizzi, R. Hlushchuk, V. Djonov, A. H. Zisch, J. A. Hubbell, F. E. Weber, M. P. Lutolf, Biomaterials 2007, 28, 3856.

[4] M. Ehrbar, S. C. Rizzi, R. G. Schoenmakers, B. San Miguel, J. A. Hubbell, F. E. Weber, M. P. Lutolf, Biomacromolecules 2007, 8, 3000.

[5] J. S. Miller, C. J. Shen, W. R. Legant, J. D. Baranski, B. L. Blakely, C. S. Chen, Biomaterials 2010, 31, 3736; M. Ehrbar, R. Schoenmakers, E. H. Christen, M. Fussenegger, W. Weber, Nat Mater 2008, 7, 800.

[6] P. S. Lienemann, M. Karlsson, A. Sala, H. M. Wischhusen, F. E. Weber, R. Zimmermann, W. Weber, M. P. Lutolf, M. Ehrbar, Advanced healthcare materials 2013, 2, 292.

[7] C. A. DeForest, B. D. Polizzotti, K. S. Anseth, Nat Mater 2009, 8, 659.

[8] R. G. Wylie, S. Ahsan, Y. Aizawa, K. L. Maxwell, C. M. Morshead, M. S. Shoichet, Nat Mater 2011, 10, 799.

[9] J. S. Miller, K. R. Stevens, M. T. Yang, B. M. Baker, D.-H. T. Nguyen, D. M. Cohen, E. Toro, A. A. Chen, P. A. Galie, X. Yu, R. Chaturvedi, S. N. Bhatia, C. S. Chen, Nat Mater 2012, 11, 768.

[10] A. Sala, P. Hanseler, A. Ranga, M. P. Lutolf, J. Voros, M. Ehrbar, F. E. Weber, Integrative Biology 2011, 3, 1102.

[11] A. M. Kloxin, A. M. Kasko, C. N. Salinas, K. S. Anseth, Science 2009, 324, 59.

[12] N. Zaari, P. Rajagopalan, S. K. Kim, A. J. Engler, J. Y. Wong, Advanced Materials 2004, 16, 2133; J. A. Burdick, A. Khademhosseini, R. Langer, Langmuir 2004, 20, 5153.

[13] B. Derby, Science 2012, 338, 921.

[14] C. Laslau, D. E. Williams, B. Kannan, J. Travas-Sejdic, Advanced Functional Materials 2011, 21, 4607; D. Bhattacharjya, I. Mukhopadhyay, Langmuir 2012, 28, 5893.

[15] S. K. Seol, J. T. Kim, J. H. Je, Y. Hwu, G. Margaritondo, Macromolecules 2008, 41, 3071.

[16] J. T. Kim, S. K. Seol, J. Pyo, J. S. Lee, J. H. Je, G. Margaritondo, Advanced Materials 2011, 23, 1968.

[17] E. De Giglio, S. Cometa, C. Satriano, L. Sabbatini, P. G. Zambonin, Journal of Biomedical Materials Research Part A 2009, 88A, 1048.

[18] S. Jegadesan, R. C. Advincula, S. Valiyaveettil, Advanced Materials 2005, 17, 1282; B. W. Maynor, S. F. Filocamo, M. W. Grinstaff, J. Liu, Journal of the American Chemical Society 2001, 124, 522.

[19] M. Gabi, T. Sannomiya, A. Larmagnac, M. Puttaswamy, J. Voros, Integrative Biology 2009, 1, 108; J. Uquillas, O. Akkus, Ann Biomed Eng 2012, 40, 1641.

[20] K. M. Chrobak, D. R. Potter, J. Tien, Microvascular Research 2006, 71, 185.

[21] M. Cordey, M. Limacher, S. Kobel, V. Taylor, M. P. Lutolf, STEM CELLS 2008, 26, 2586.

[22] M. P. Lutolf, J. A. Hubbell, Biomacromolecules 2003, 4, 713.

[23] J. C. Schense, J. A. Hubbell, Bioconjugate Chemistry 1998, 10, 75.

[24] B.-H. Hu, P. B. Messersmith, Journal of the American Chemical Society 2003, 125, 14298.

[25] M. P. Lutolf, N. Tirelli, S. Cerritelli, L. Cavalli, J. A. Hubbell, Bioconjugate Chemistry 2001, 12, 1051.

[26] I. F. Sbalzarini, P. Koumoutsakos, Journal of Structural Biology 2005, 151, 182.

The invention claimed is:

1. A method for controlling a linking reaction in a solution in proximity of a first electrode (11), wherein a spatially-structured hydrogel (200) is formed by said linking reaction, the method comprising:
providing a solution in which a linking reaction is to occur in proximity to a first electrode, wherein the linking reaction is the formation of a covalent bond; and
applying an electrolysis-inducing electrical current to said solution via said first electrode; thereby
locally altering the pH of the of the solution in the proximity of said electrode (11) and
inhibiting the enzymatic activity of an enzyme in the solution that forms a covalent bond between a first and a second moiety (21, 23) comprised by a first and a second compound (20, 22) in the solution in order to form said hydrogel (200),
thereby controlling said linking reaction.

2. The method according to claim 1, characterized in that the linking reaction is spatially and/or temporally confined by altering the electrical current flowing through the solution.

3. The method according to claim 1, characterized in that said enzyme is an aminoacyltransferase.

4. The method according to claim 1, characterized in that the first and/or second compound comprises a a natural polymer.

5. The method according to claim 1, characterized in that the first compound (20) and/or the second compound (22) comprises polyethyleneglycol (PEG).

6. The method according to claim 1, characterized in that the formation of the covalent bond is a condensation reaction, a linking reaction, a ligation reaction, a cross-linking reaction or a polymerization reaction.

7. The method according to claim 1, characterized in that a voltage is induced via electrodes (11, 12) in said solution.

8. The method according to claim 1, characterized in that the enzymatic activity of the enzyme is locally inhibited or reduced depending on the voltage applied to the solution.

9. The method according to claim 1, characterized in that the solution comprises a third compound (24, 25) comprising a third moiety wherein said third moiety is convertible by said enzyme with the respective first or second moiety.

10. The method according to claim 1, characterized in that one or several parameters of the linking reaction are changed during the linking reaction, wherein at least one of the following parameters is changed during the linking reaction:
the composition buffer, enzymes, substrate of the enzyme, the used polymers and/or their functional groups,
the position of the first and/or second electrode,
the applied current or voltage, and/or
the duration of the linking reaction.

11. The method according to claim 1, characterized in that the duration of the linking reaction is interrupted.

* * * * *